United States Patent [19]

Alpegiani et al.

[11] Patent Number: 4,585,874

[45] Date of Patent: Apr. 29, 1986

[54] PROCESS FOR PREPARING PENEM DERIVATIVES

[75] Inventors: Marco Alpegiani; Angelo Bedeschi; Maurizio Foglio; Giovanni Franceschi; Ettore Perrone, all of Milan, Italy

[73] Assignee: Farmitalia Carlo Erba S.p.A., Milan, Italy

[21] Appl. No.: 558,629

[22] Filed: Dec. 6, 1983

[30] Foreign Application Priority Data

Dec. 8, 1982 [GB] United Kingdom ................. 8235058
Aug. 27, 1983 [GB] United Kingdom ................. 8323129

[51] Int. Cl.[4] ........................................... C07D 499/00
[52] U.S. Cl. .................................... 546/272; 514/192;
514/195; 260/245.2 R; 260/245.2 T; 260/239 A
[58] Field of Search ................. 260/245.2 R, 245.2 T;
546/272; 514/192, 195, 196

[56] References Cited

U.S. PATENT DOCUMENTS 4,474,793 10/1984 Ross et al. ................... 260/245.2 R
4,485,110 11/1984 Osborne ....................... 260/245.2 R
4,496,684 1/1985 Micetich et al. ............. 260/245.2 R Primary Examiner—Nicholas S. Rizzo
Attorney, Agent, or Firm—Oblon, Fisher, Spivak, McClelland & Maier

[57] ABSTRACT

A new process is described for the preparation of (5R)-penem derivatives of the general formula I:

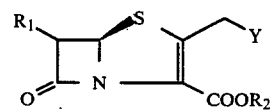

wherein $R_1$ represents a hydrogen atom or an organic group; $R_2$ represents a hydrogen atom or a carboxy protecting group and Y represents a hydrogen or halogen atom or an organic group. A 2-thiacephem derivative of the general formula II:

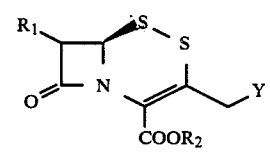

wherein $R_1$, $R_2$ and Y have the meanings given above is oxidized by means of organic peracids to the corresponding sulphone of the general formula III:

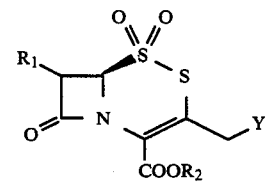

which is subsequently submitted to a desulphurative ring contraction by extrusion of $SO_2$ to give exclusively the desired (5R)-penem derivatives of the general formula I.

14 Claims, No Drawings

PROCESS FOR PREPARING PENEM DERIVATIVES

DESCRIPTION

The invention relates to a new process for the preparation of (5R) penem compounds of the general formula I and their pharmaceutically and/or veterinarily acceptable salts.

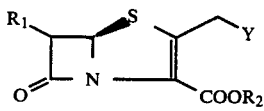

In the general formula I, $R_1$ represents a hydrogen atom or an organic group; $R_2$ represents a hydrogen atom or a carboxy protecting group; and Y represents a hydrogen or halogen atom or an organic group.

Organic groups which $R_1$ may represent include optionally substituted aliphatic or cycloaliphatic groups. The aliphatic groups are preferably alkyl groups having from 1 to 12 carbon atoms and the optional substituents may be one or more hydroxy, amino, cyano and/or mercapto groups. The hydroxy, amino and mercapto groups may be free or protected. Particularly preferred alkyl groups are methyl and ethyl, especially the latter, and a preferred sustituent for such a group is a hydroxy group, which may be free or protected. The 1-hydroxylethyl group in 6S, 8R or 6R, 8S configuration is most preferred. The cycloaliphatic groups are preferably monocycloalkyl groups having from 4 to 7 carbon atoms. Cyclopentyl and cyclohexyl groups are especially preferred. Optional substituents are preferably chosen from alkyl groups having from 1 to 6 carbon atoms, for example methyl or ethyl groups, hydroxy, amino and mercapto groups, the hydroxy, amino and mercapto groups being free or protected.

The carboxy protecting group $R_2$ may be any group which, together with the —COO—moiety, forms an esterified carboxy group. Examples of carboxy protecting groups $R_2$ are, in particular, alkyl groups having from 1 to 6 carbon atoms, for instance methyl, ethyl or t-butyl; halo-substituted alkyl groups having from 1 to 6 carbon atoms, for example 2,2,2-trichloroethyl; alkenyl groups having from 2 to 4 carbon atoms for example allyl; optionally substituted aryl groups, for example phenyl and p-nitro-phenyl; aryl substituted alkyl groups, the alkyl part whereof has from 1 to 6 carbon atoms and the aryl part whereof is optionally substituted, for example, benzyl, p-nitro-benzyl and p-methoxy-benzyl; aryloxy substituted alkyl groups, the alkyl part whereof has from 1 to 6 carbon atoms, for example phenoxy-methyl; or groups such as benzhydryl, o-nitro-benzhydryl, acetonyl, trimethylsilyl, diphenyl-t-butyl-silyl, and dimethyl-t-butyl-silyl. The definition of $R_2$ as a carboxy protecting group also includes any residue, such as acetoxymethyl, pivaloyloxymethyl or phthalidyl, leading to an ester group which is known to be hydrolyzed "in vivo" and to have favourably pharmacokinetic properties.

When Y represents a halogen atom, it is preferably a fluorine, chlorine or bromine atom. When Y represents an organic group, it is preferably (a) a free or protected hydroxyl group;

(b) a formyloxy group or an acyloxy group having from 2 to 6 carbon atoms, optionally substituted by a halogen atom, by an acyl groop having from 2 to 6 carbon atoms, or by an amino, hydroxy or mercapto group, the amino, hydroxy or mercapto group optionally being in a protected form;

(c) an unsubstituted or N-alkyl substituted carbamoyloxy group;

(d) an alkoxy group having from 1 to 12 carbon atoms or an alkylthio group having from 1 to 12 carbon atoms, either of which is optionally substituted by one or more halogen atoms, formyl groups, acyl groups having from 2 to 6 carbon atoms, and/or amino, hydroxy or mercapto groups, the amino, hydroxy or mercapto group optionally being in a protected form;

(e) a 1-pyridinium group, unsubstituted or substituted in the meta or para position with the group —CONH$_2$;

(f) a heterocyclylthio group —S—Het wherein Het, denoting a saturated or unsaturated heterocyclic ring containing at least one oxygen, sulphur and/or nitrogen heteroatom, is preferably:

(A) a pentatomic or hexatomic heteromonocyclic ring, containing at least one double bond and at least one oxygen, sulphur and/or nitrogen heteroatom, unsubstituted or substituted by one or more (a') alkoxy groups having from 1 to 6 carbon atoms, aliphatic acyl groups having from 2 to 6 carbon atoms, hydroxy groups and/or halogen atoms;

(b') alkyl groups having from 1 to 6 carbon atoms, unsubstituted or substituted by one or more hydroxy groups and/or halogen atoms;

(c') alkenyl groups having from 2 to 6 carbon atoms, unsubstituted or substituted by one or more hydroxy groups and/or halogen atoms;

(d') groups of the general formula —S—$R_3$ wherein $R_3$ represents a hydrogen atom or an alkyl group having from 1 to 6 carbon atoms, or groups of the general formula —S—CH$_2$—COOR$_4$ wherein $R_4$ represents a hydrogen atom, an alkyl group having from 1 to 6 carbon atoms or a carboxy-protecting group;

(e') groups of the general formula —(CH$_2$)$_m$—COOR$_4$ or —CH=CH—COOR$_4$ or —(CH$_2$)$_m$—CN or —(CH$_2$)$_m$—CONH$_2$ or —(CH$_2$)$_m$—SO$_3$H wherein m is zero, 1, 2 or 3 and $R_4$ is as defined above;

(f') groups of the general formula

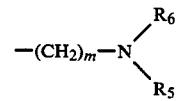

wherein m is as defined above, and each of $R_5$ and $R_6$, which may be the same or different, represents a hydrogen atom, an alkyl group having from 1 to 6 carbon atoms or an aliphatic acyl group or when one of $R_5$ and $R_6$ is hydrogen, the other may be also an amino protecting group; or (B) a heterobicyclic ring, containing at least two double bonds wherein each of the condensed heteromonocyclic rings, being the same or different, is a pentatomic or hexatomic heteromonocyclic ring containing at least one oxygen, sulphur or nitrogen hetroatom, said heterobicyclic ring being unsubstituted or substituted by one or more substituents selected form (a'), (b'), (c'), (e') and (f') as defined above.

In the above definitions (A) and (B) preferred halogens are chlorine, bromine and iodine; preferred alkyl groups are methyl and ethyl; a preferred alkenyl group is allyl; a preferred aliphatic acyl group is acetyl; a carboxy protecting group may be any of the groups previously indicated for the $R_2$ substituent; and the free sulpho and carboxy groups possibly present may be salified, e.g. as sodium or potassium salts. A heteromonocyclic ring of the above class (A) may be, for example, an optionally substituted thiazolyl, triazolyl, thiadiazolyl, tetrazolyl or triazinyl ring. Preferred substituents on such rings are, for example, one or more substituents chosen from amino, hydroxy, oxo and a $C_1$-$C_6$-alkyl group preferably methyl or ethyl, wherein the $C_1$-$C_6$-alkyl group may be optionally substituted by a substituent chosen from carboxy, sulpho, cyano, carbamoyl, amino, methylamino or dimethylamino. A heterobicyclic ring of the above class (B) may be for example, a tetrazolopyridazinyl radical optionally substituted by amino or carboxy.

In the above formula I the amino, hydroxy or mercapto protecting groups possibly present may be those usually employed in the chemistry of penicillins and cephalosporins for these functions. They may be, for instance optionally substituted, especially halo-substituted, acyl groups, e.g. acetyl, monochloroacetyl, dichloroacetyl, trifluoroacetyl, benzoyl or p-bromophenacyl; triarylmethyl groups, in particular triphenylmethyl; silyl groups, in particular trimethylsilyl, dimethyl-t-butyl-silyl, diphenyl-t-butyl silyl- or also groups such as t-butoxycarbonyl, p-nitrobenzyloxycarbonyl, 2,2,2-trichloroethoxycarbonyl, benzyl, pyranyl and nitro. When, in particular, the $R_1$ substituent in formula (I) is a hydroxyalkyl group, preferred protecting groups for the hydroxy function are p-nitro-benzyloxycarbonyl; dimethyl-t-butyl-silyl-; diphenyl-t-butylsilyl; trimethylsilyl; 2,2,2-trichloroethoxycarbonyl; benzyl; p-bromo-phenacyl; triphenylmethyl and pyranyl. All the alkyl and alkenyl groups, including the aliphatic hydrocarbon moiety of the alkoxy, alkyl thio and acyloxy groups, may be branched or straight.

The pharmaceutically and/or veterinarily acceptable salts may be both salts with acids, either inorganic acids such as hydrochloric or sulphuric acid, or organic acids such as citric, tartaric, fumaric or methanesulphonic acid, and salts with bases, either inorganic bases such as alkali metal or alkaline-earth metal hydroxides, in particular sodium and potassium hydroxides, or organic bases such as triethylamine, pyridine, benzylamine or collidine. Preferred salts are the salts of the compounds of formula I wherein $R_2$ represents a hydrogen atom with one of the bases hereabove specified in particular with sodium hydroxide or potassium hydroxide.

The compounds of the general formula I obtainable by the process of the invention are known compounds, described and claimed in our British Patent Specifications Nos. 2043639A and 8210410. They are potent, broad-spectrum antimicrobial agents, and are therefore useful in the treatment of bacterial infections in warm-blooded animals, especially in humans, by enteral or parenteral administration.

Desulphurative ring contraction of 2-thiacephem of the general formula II

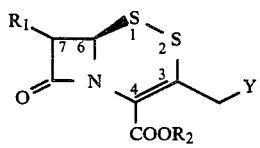

wherein $R_1$, $R_2$ and Y are as above defined is a known process for the preparation of penems, but it suffers from poor or adverse stereoselectivity. Although the carbon atom in position 6 has the R configuration, the desulphurization usually gives (5S)-penems which are biologically inactive (H. R. Pfaendler et al., J. Am. Chem. Soc., 101, 1979, 6306) or a mixture of (5S)- and (5R)-penems (A. Henderson et al., J. Chem. Soc. Commun., 1982, 809). We have found and described in Tetrahedron Letters, 24, pag. 3283 (1983) that (5R)-penems can be obtained from such desulphurative ring contractions if the substituents $R_1$, $R_2$ and Y and the solvent for the process are suitably selected. A more general stereoselective process, operable over the full range of values of the substituents $R_1$, $R_2$ and Y is, however, clearly desirable, as it would obviate the losses involved in the formation of the undesired (5S)-isomers and their separation from the desired (5R)-isomers.

The invention provides a process for the preparation of a (5R) penem having the general formula I as above defined, the process comprising oxidising a 2-thiacephem having the general formula II as above defined and wherein the carbon at position 6 has the R configuration to give a sulphone having the general formula III

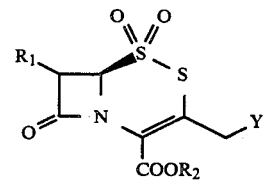

wherein $R_1$, $R_2$ and Y are as above defined, and ring contracting the sulphone by extrusion of sulphur dioxide; and, if desired, converting the resultant (5R) penem of the general formula I into another compound of the general formula I; and/or, if desired, converting the resultant compound of the general formula into a salt thereof; and/or, if desired, obtaining a free compound of the general formula I from a salt thereof.

The oxidation may be carried out using oxidizing agents usually used to convert an organic sulphide into the corresponding sulphone. Preferred oxidizing agents are peracids such as m-chloroperbenzoic acid or peracetic acid. The reaction is generally performed in an inert solvent at a temperature of from 0° to 60° C., preferably from 4° to 30° C.

The ring contraction of the sulphone, with loss of sulphur dioxide, may be effected simply by heating it in an inert organic solvent such as chloroform or benzene. The ring contraction may, in some cases, even occur spontaneously at room temperature. The R configuration of the carbon atom in position 6 in the 2-thiacephem II is retained throughout the process, so that (5R)-penems are obtained exclusively. It is noteworthy that, although loss of sulphur dioxide from thiosulphonates has occasionally been reported. (see, for example, W. L. F. Armarego and E. E. Turner, J. Chem. Soc. 1956, 1665; A. Padwa and R. Gruber, J. Org. Chem. 35, 1970, 1781), this reaction has hardly any precedent as yields and mildness of operative conditions are concerned and for the first time it has been applied in the synthesis of β-lactam compounds. The present invention also provides routes to obtain the required compounds of formula II possessing the (5R) configuration.

According to the invention, the compounds of the general formula II are prepared by either of the routes shown in the following reaction scheme wherein:

R₁, R₂ and Y are as defined above,

Z represents (i) a group of the formula SR₇ wherein R₇ represents an alkyl group having from 1 to 8 carbon atoms, a phenyl or tolyl group, or, preferably, a heterocyclic group, especially a 2-benzothiazolylthio or 1-methyl-tetrazol-5-yl-thio group, (ii) a group of the formula SCOR₈ wherein R₈ represents an optionally substituted lower alkyl group, preferably a methyl group, (iii) a group of the formula

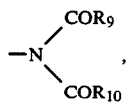

wherein R₉ and R₁₀ independently represent lower alkyl or aryl groups, or together with the dicarboxyamino group form a heterocyclic ring, preferably a succinimido or phthalimido group, or (iv) a group of the formula

wherein R₁₁ represents an optionally substituted lower alkyl or aryl group, preferably a methyl, phenyl or p-tolyl group; and L represents a halogen atom, an alkane sulphonyloxy group or an arene sulphonyloxy group, preferably a methanesulphonyloxy group.

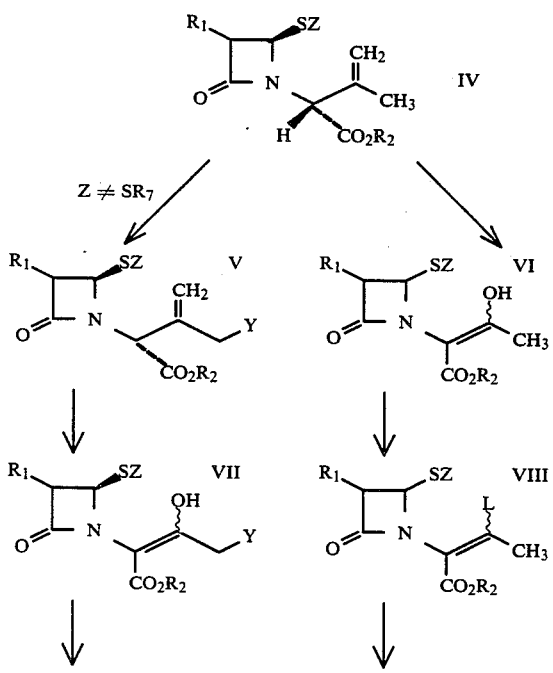

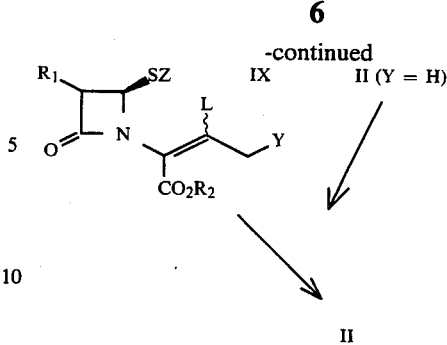

Compounds of the general formula IV, which are used as starting materials, are known compounds or can be obtained from known compounds by per se known procedures; the preparation of some representative entries is described in the Examples.

The compound of the general formula IV is first ozonolysed to give a compound of the general formula VI. The hydroxy group is then converted into a group L and the resultant compound of the general formula VIII is cyclised to give a compound of the general formula II in which Y represents a hydrogen atom. If desired, the methyl group may then be halogenated to give a compound of the general formula II in which Y represents a halogen atom.

In an alternative process, the compound of the general formula IV may first be halogenated by methods known per se (allyl,ene-type, or electrochemical halogenation, see Tetrahedron Letters, 1980, 71 and 351; 1981, 3193; 1982, 2187). The resultant compound of the general formula V is then ozonolysed; the hydroxy group of the resultant compound of the general formula VII is then transformed into a group L and the resultant compound of the general formula IX is cyclised to give a compound of the general formula II.

The group Y in the compounds of the general formulae V, VII, IX and II may, if it represents a halogen atom, be optionally transformed into any of the other groups which Y may represent except a hydrogen atom. According to a preferred feature of the invention, this transformation is preferably carried out on the compounds of the general formula II.

The transformation into a group L of the hydroxy group in the enol VI or VIII, which may be in equilibrium with the corresponding keto-tautomer, is preferably a mesylation. We have surprisingly found that, when this reaction is carried out in tetrahydrofuran instead of the ubiquitously used halogenated hydrocarbons, mesylates IX or VIII having Z alkene geometry, which are the most suitable ones for the subsequent cyclization, are almost exclusively obtained (similar transformation performed in dichloromethane usually affords a 1:1 mixture of E, Z isomers: see T. W. Doyle, et al. Can. J. Chem. 1977, 55, 2873; M. J. Pearson, J. Chem. Soc., Chem. Comm. 1981, 947; P. C. Cherry et al. J. Chem. Soc., Chem. Comm. 1979 663). Cyclisation of VIII or IX may be carried out in a single step, by reaction with a sulphide or hydrosulphide, such as Na₂S, NaHS, Bu₄NHS, or with H₂S in the presence of a base such as triethylamine or pyridine. The cyclisation of IX or VIII wherein Z represents a group other than SR₇ offers the clear advantage of releasing easily separable, usually water soluble by-products ZH (e.g. phenylsulphinic acid, succinimide), instead of by products R₃SH (e.g. mercaptobenzthiazole) which usually require chromatographic separation or precipitation as heavy metal salts (Ag+, Pb2+).

Against any reasonable expectation, which would rule out the possibility of halogenating the 3-methyl group of the compounds II (Y=H) owing to the presence of the disulphide moiety, we have found a method to effect such transformation in high yield. We can thus obtain the compounds II (Y=halogen), which are invaluable intermediates for the synthesis of highly active penem antibiotics I. A preferred halogenating reagent for such transformation is N-bromosuccinimide, which is best used in the presence of a radical initiator, such as azobisisobutyronitrile or benzoyl peroxide in the presence of acid scavengers, such as epoxides (e.g. propylene oxide, alkaline-earth oxides, (e.g. calcium oxide), or molecular sieves, in solvents such as benzene or carbon tetrachloride, ethyl formate at a temperature ranging from 20° C. to 130° C.

The compounds II (Y=halogen) can be converted into compounds II (Y=an organic group) by reactions known per se; e.g.

(1) A compound II (Y=Br or Cl) can be converted into a compound II (Y=free or protected OH) by mild alkaline hydrolysis, or by reaction with cuprous oxide/-dimethylsulphoxide/water or by reaction with a salt of a strong inorganic acid, e.g. a nitrate or a perchlorate, thus obtaining a labile ester with the said inorganic acid, which ester may be hydrolyzed, subsequently or in the same reaction medium, to the desired parent alcohol. Preferred salts of this type are AgNO3, AgClO4, NaNO3;

(2) A compound II (Y=Br or Cl) can be converted into a compound II (Y=an unsubstituted or N-alkyl substituted carbamoyloxy group) by conversion into a compound of II (Y=OH) as described above followed by reaction with a suitable isocyanate; for example, trichloroacetyl isocyanate is a preferred reagent for obtaining compounds II (Y=OCONH2), following deprotection of the trichloroacetyl moiety on the first formed urethane adduct;

(3) a compound II (Y=Br or Cl) can be converted into a compound II (Y=acyloxy) by reaction with a suitable salt of the corresponding carboxylic acid in a suitable solvent or under phase-transfer catalysis; or by conversion into a compound II (Y=OH) followed by conventional acylation;

(4) a compound II (Y=Br or Cl) can be converted into a compound II (Y=S-Het) by reaction with the corresponding HS-Het in the presence of a base, or with a preformed salt of HS-Het with a base, in a suitable solvent, such as tetrahydrofuran, acetone, acetonitrile or dimethylformamide. A suitable base is triethylamine; a suitable preformed salt is a sodium salt, e.g. sodium 1-methyl-1,2,3,4-tetrazol-5-yl-mercaptide.

Owing to the pronounced propensity of 3-hydroxymethyl-2-thiacephem-4-carboxylates to lactonize, it is preferable that in the process (1) described above R2 represents a somewhat bulky group, forming with the linked carboxy moiety an ester possessing a relative inertness towards nucleophilic attack by the neighbouring hydroxy group, e.g. a tert-butyl ester. Alternatively, it may be convenient to deprotect the hydroxy group from a protected form thereof after the ring-contraction step to the corresponding penem I, since 2-hydroxymethylpenemcarboxylates do not lactonize easily. For example, a compound II (Y=Br) may be converted into a compound II (Y=ONO2), which may easily be isolated, purified if necessary, desulphurized to the corresponding penem I whose reductive hydrolysis (e.g. Zn/CH3COOH) affords without problems the free hydroxy derivative.

Owing to the different stability of the penem and 2-thiacephem nucleus towards the condition required for —COOR2 ester hydrolysis, a distinct advantage of the invention is that ester hydrolyses not compatible with a penem can be performed on the 2-thiacephem precursor, and the ring contraction may be performed on the free acid, or on a salt with an organic or inorganic base, or on a different labile ester, which ca be prepared in situ, if desired; e.g. a trimethylsilyl, t-butyldimethylsilyl, or t-butyldiphenylsilyl ester.

The following Examples illustrate the invention. The abbreviations Me, Bu$^t$, Ph, Ms, pNB, THF, EtOAc, DMSO, MeCN, stand respectively for methyl, t-butyl, phenyl, methansulphonyl, p-nitrobenzyl, tetrahydrofuran, ethyl acetate, dimethylsulphoxide and acetonitrile. NMR spectra were taken either on a Hitachi-Perkin Elmer 60 MHz apparatus, or on a Brucker 90 MHz; separation of inner lines of AB quartets are referred to spectra taken on the latter.

EXAMPLE 1

Diphenylmethyl 6,6-dibromopenicillanate

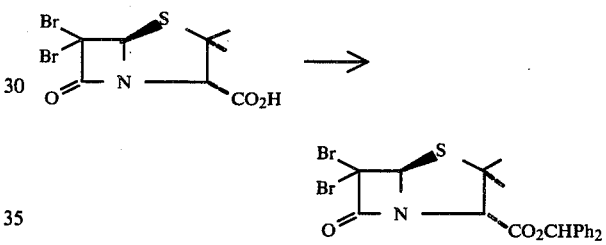

6,6-Dibromopenicillanic acid (90 g) in acetonitrile (450 ml) was treated with a solution of diphenyldiazomethane (49 g) in the same solvent (150 ml). After 1 hour at 20° C. the formed solid was collected by filtration and washed with small portions of cold ethyl ether, thus obtaining 116 g of title product. A second crop (9 g) was obtained by evaporation of the mother liquors and trituration with ethyl ether; yield 95%.

An analytical sample was obtained by crystallization from chloroform; mp 157°-158°; $\gamma_{max}$ (CHCl3 film) 1800, 1750 cm$^{-1}$; δ (CDCl3) 1.24 and 1.58 (each 3H, s, CMe2), 4.61 (1H, s, N.CH.CO), 5.80 (1H, s, N.CH.S), 6.91 (1H, s, OCH), and 7.30 ppm (10H, s, Ar). Found: C, 47.80; H, 3.63; N, 2.64; S, 5.95; Br, 30.49%. C21H19Br2NO3S requires C, 48.02; H, 3.64; N, 2.67; S, 6.10; Br, 30.43%.

EXAMPLE 2

Tert-butyl 6,6-dibromopenicillanate

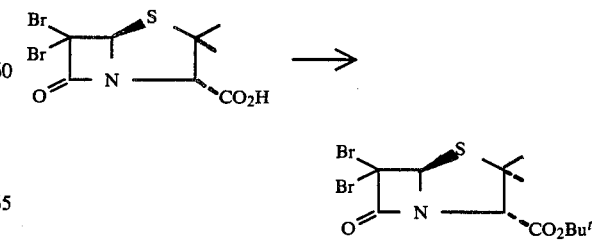

(Method A)

6,6-Dibromopenicillanic acid (100 g) in ethyl ether (1 l) at 0° C. was sequentially treated with triethylamine (37 ml) and PCl$_5$ (56 g). After 1 hour stirring, the reaction mixture was evaporated under vacuum (dry benzene added and removed) and the crude acyl chloride dissolved in dichloromethane (200 ml) and stirred for 24 hours with tert-butanol (500 ml) in the presence of CaCO$_3$ (50 g). The suspended salts were then filtered off and the solution was washed with aqueous NaHCO$_3$ (some unreacted starting material could be recovered by back-extraction of the acidified aqueous washings), decolorized with charcoal and evaporated to afford the title product, which was then crystallized from diisopropyl ether, 69 g (60%); mp 120°–121° C., $\gamma_{max}$ (CHCl$_3$ film) 1800 and 1740 cm$^{-1}$; δ (CDCl$_3$) 1.98 (15H, s, Bu$^t$ and CH$_3$), 2.05 (3H, s, CH$_3$), 4.38 (1H, s, N.CH.CO), and 5.70 (1H, s, N.CH.S) ppm.

Method (B)

6,6-Dibromopenicillanic acid (15 g) in dichloromethane (300 ml) was stirred overnight with O-tert-butyl-N,N-diisopropyl-isourea (25 g). The reaction mixture was filtered and the solution washed with aqueous NaHCO$_3$. Crystallization of the product from diisopropyl ether gave the title compound, 8 g (47%).

EXAMPLE 3

Diphenylmethyl 6α-bromo-6β-[1(R)-hydroxyethyl]-penicillanate

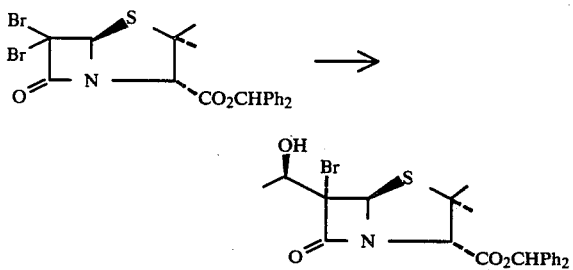

Diphenylmethyl 6,6-dibromopenicillanate (120 g) in dry distilled THF (900 ml) under nitrogen at −75° C. was treated with a solution of ethylmagnesium bromide in ethyl ether (1 molar equivalent). After 20 min at −75° C., acetaldehyde (25.7 ml) was added and the mixture further stirred for 20 min at −75° C. After quenching with saturated aqueous NH$_4$Cl (400 ml), partition between water and ethyl ether, followed by removal of the solvent, left the crude product which was fractionated by silica gel chromatography (benzene-ethyl acetate) to afford the title compound, 67 g (60%), as a foam, crystallizable (diisopropyl ether) to a solid, mp 65°–70°; $\gamma_{max}$ (film) 3450, 1785 and 1740 cm$^{-1}$; δ (CDCl$_3$) 1.22 and 1.60 (each 3H, s, CMe$_2$), 1.29 (3H, d, J=6 Hz, CH$_3$.CH), 2.90 (1H, d, OH), 4.17 (1H, m, CH$_3$.CH.OH), 4.58 (1H, s, N.CH.CO), 5.49 (1H, s, N.CH.S), 6.90 (1H, s, OCHPh$_2$), and 7.3 (10H, s, Ar) ppm.

By using a similar procedure, and starting from tert-butyl 6,6-dibromopenicillanate, there was obtained tert-butyl 6α-bromo-6β-[1(R)-hydroxyethyl]-penicillanate in 65% yield after crystallization from diisopropylether/hexane; mp 93°–95° C. (dec); δ (CDCl$_3$) 1.28 (3H, d, J=6 Hz, CH$_3$.CH), 1.54 (12H, s, Bu$^t$ and CH$_3$), 1.65 (3H, s, CH$_3$), 2.65 (1H, s, CH.OH), 4.25 (1H, m, CH$_3$.CH(OH).CH), 4.40 (1H, s, N-CH.CO), and 5.51 ppm (1H, s, N.CH.S).

EXAMPLE 4

Diphenylmethyl 6α-[1(R)-hydroxyethyl]-penicillanate-1-oxide

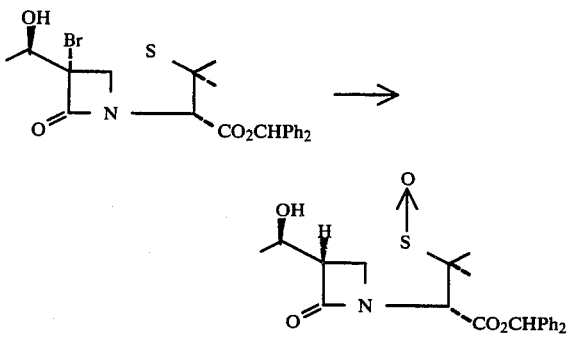

Diphenylmethyl 6α-bromo-6β-[1(R)-hydroxyethyl]-penicillanate (52 g) in 95% ethanol (400 ml) was hydrogenated at 30 Psi in the presence of 10% Pd/CaCO$_3$ (25 g) and CaCO$_3$ (11 g). The reaction mixture was filtered and evaporated to afford a residue which was partitioned between brine and dichloromethane. Removal of the solvent left crude diphenylmethyl 6α-[1(R)-hydroxyethyl]-penicillanate, which was oxidized with 85% MCPBA (17 g) in 500 ml of chloroform at 0°–5° C. for 1 hour. The filtered solution was then washed with aqueous NaHCO$_3$ and the solvent removed to leave the crude title product as a foam, 40 g (88%), which can be used as such or purified by silica gel chromatography; $\gamma_{max}$ (CHCl$_3$ film) 1790 and 1750 cm$^{-1}$; δ (CDCl$_3$) 0.94 and 1.67 (each 3H, s, CMe$_2$), 1.37 (3H, d, J=6 Hz), 3.55 (1H, dd, J=2 and 6.5 Hz, CH.CH.CH), 4.25 (1H, m, CH$_3$.CH(OH).CH), 4.64 (1H, s, N.CH.CO), 4.98 (1H, d, J=2 Hz, CH.CH.S), 6.98 (1H, s, OCHPh$_2$), and 7.30 (10H, s, Ar) ppm.

By using a similar procedure, and starting from tert-butyl 6α-bromo-6β-[1(R)-hydroxyethyl]-penicillanate, there was obtained (75%) tert-butyl 6-[1(R)-hydroxyethyl]-penicillanate-1-oxide; $\gamma_{max}$ (film) 3440, 1785 and 1740 cm$^{-1}$.

EXAMPLE 5

Diphenylmethyl 6α-[1(R)-tert-butyldimethylsilyloxyethyl]-penicillanate-1-oxide

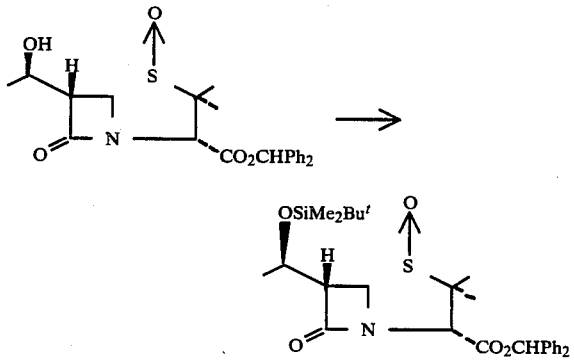

Crude diphenylmethyl 6α-[1(R)-hydroxyethyl]-penicillanate -1-oxide, as obtained in Example 4 (40 g), was dissolved in DMF (350 ml) and stirred for 3 hours at 50°–55° C. in the presence of imidazole (18.5 g) and tert-butyldimethylsilylchloride (27 g). The reaction mixture was partitioned between ethyl ether and brine and the organic layer washed several times with water. Evaporation of the solvent and silica gel chromatography afforded the title product, 22 g; $\gamma_{max}$ (CHCl$_3$ film) 1790 and 1755 cm$^{-1}$; δ (CDCl$_3$) 0.06 (6H, s, SiMe$_2$), 0.88 (13H, s, Bu$^t$ and CH$_3$), 1.3 (3H, d, J=6 Hz, CH$_3$.CH), 1.7 (3H, s, CH$_3$), 3.4 (1H, dd, J=2 and 4.5 Hz, CH.CH.CH), 4.40 (1H, m, CH$_3$.CH.CH), 4.55 (1H, s, N.CH.CO), 4.88 (1H, d, J=2, CH.CH.S), 6.9 (1H, s, OCHPh$_2$), and 7.25 ppm (10H, s, Ar).

By using a similar procedure and starting from tert-butyl 6α-[1(R)-hydroxyethyl]-penicillanate-1-oxide, there was obtained tert-butyl 6-[1(R)-tert-butyldimethylsilyloxyethyl]-penicillanate-1-oxide in overall 55% from the 6α-bromo precursor; $\gamma_{max}$ (CHCl$_3$ film) 1785 and 1750 cm$^{-1}$; δ (CDCl$_3$) 0.06 (6H, s, SiMe$_2$), 0.88 (9H, s, SiBu$^t$), 1.25 and 1.66 (each 3H, s, CMe$_2$), 1.28 (3H, d, J=6 Hz, CH$_3$.CH), 1.45 (9H, s, OBu$^t$), 3.5 (1H, dd, J=2 and 5 Hz, CH.CH.CH), 4.4 (1H, s, N.CH.CO), 4.5 1H, m, CH$_3$.CH.CH), and 4.9 ppm (1H, d, J=2 Hz, CH.CH.S)

EXAMPLE 6

Diphenylmethyl 6α-[(R)-p-nitrobenzyloxycarbonyloxyethyl]-penicillanate-1-oxide

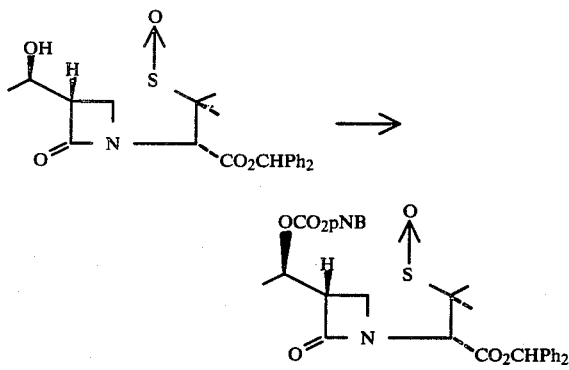

Diphenylmethyl 6α-[1(R)-hydroxyethyl]-penicillanate-1-oxide was acylated with p-nitrobenzylchlorocarbonate by using N,N-dimethylaminopyridine as a base and ethanol-free dichloromethane as solvent, according to a general method, thus obtaining the title product as a foam; δ (CDCl$_3$) 0.96 and 1.70 (each 3H, s, CMe$_2$), 1.52 (3H, d, J=6 Hz, CH$_3$.CH), 3.83 (1H, dd, J=2 and 6 Hz, CH.CH.CH), 4.66 (1H, s, N.CH.CO), 4.99 (1H, d, J=2 Hz, CH.CH.S), 5.28 (2H, s, OCH$_2$Ph), 5.35 (1H, m, CH$_3$.CH.CH), 7.01 (1H, s, OCHPh$_2$), 7.40 (10H, m, Ar), 7.55 and 8.26 ppm (each 2H, d, J=8 Hz, Ar).

By following the same experimental procedure, there was obtained tert-butyl 6α-[1(R)-p-nitrobenzyloxycarbonyloxyethyl]penicillanate-1-oxide By following similar experimental procedures, and using trichloroethylchlorocarbonate instead of p-nitrobenzylchlorocarbonate, these were also obtained:
tert-butyl 6α-[1(R)-p-nitrobenzyloxycarbonyloxyethyl]-penicillanate-1-oxide
diphenylmethyl 6α-[1(R)-p-nitrobenzyloxycarbonyloxyethyl]-penicillanate-1-oxide

EXAMPLE 7

3(S)-[1(R)-hydroxyethyl]-4(R)-benzthiazolyldithio-1-(1-methoxycarbonyl-2-methyl-1-prop-2-enyl)-azetidin-2-one

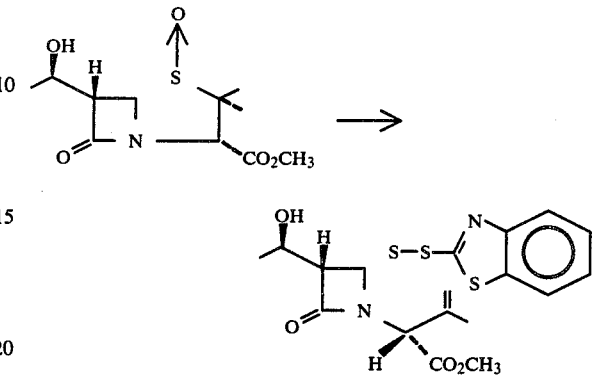

A mixture of methyl 6α-[1(R)-hydroxyethyl]-penicillanate -1-oxide (5 g) and 2-mercaptobenzthiazole (3.04 g) was refluxed for 2 h in dry toluene. The solvent was removed in vacuo and the crude product used as such for the next step.

By using a similar procedure, there were obtained:
3(S)-[1(R)-tert-butyldimethylsilyloxyethyl]-4(R)-benzthiazolyl-1-(1-methoxycarbonyl-2-methyl-1-prop-2-enyl)-azetidin-2-one, starting from methyl 6α-[1(R)-tert-butyl-dimethylsilyloxyethyl]-penicillanate-1-oxide, and prolonging the reaction time up to 6 h; $\gamma_{max}$ (CHCl$_3$ film) 1770 and 1744 cm$^{-1}$; δ (CDCl$_3$) 0.02 and 0.04 (each 3H, s, SiMe$_2$) 0.84 (9H, s, SiBu$^t$), 1.23 (3H, d, J=6 Hz, CH$_3$.CH), 1.91 (3H, s, =C.CH$_3$), 3.38 (1H, dd, J=2 and 3.5 Hz, CH.CH.CH), 3.69 (3H, s, OCH$_3$), 4.23 (1H, m, CH$_3$.CH.CH), 4.82 (1H, s, N.CH.CO), 5.07 (2H, m, CH$_2$=C), 5.42 (1H, d, J=2 Hz, CH.CH.S), and 7.2–7.9 ppm (4H, m, Ar);
3(S)-[1(R)-hydroxyethyl]-4(R)-benzthiazolyldithio-1-(1-diphenylmethoxycarbonyl-2-methyl-1-prop-2-enyl)-azetidin-2-one, starting from diphenylmethyl 6α-[1(R)-hydroxyethyl]-penicillanate-1-oxide; $\gamma_{max}$ (CHCl$_3$ film) 3400, 1765 and 1740 cm$^{-1}$; δ (CDCl$_3$) 1.22 (3H, d, J=6 Hz, CH$_3$.CH), 1.60 (3H, s, =C.CH$_3$), 2.78 (1H, br s, OH), 3.42 (1H, dd, J=2 and 6 Hz, CH.CH.CH), 4.18 (1H, m, CH$_3$.CHOH.CH), 4.93 (1H, s, N.CH.CO), 4.90–5.10 (2H, m, CH$_2$=C), 5.38 (1H, d, J=2 Hz, CH.CH.S), 6.89 (1H, s, OCHPh$_2$), and 7.15–7.90 ppm (14H, m, Ar);
3(S)-[1(R)-tert-butyldimethylsilyloxyethyl]-4(R)-benzthiazolyldithio-1-(1-tert-butoxycarbonyl-2-methyl-1-prop-2-enyl)-azetidin-2-one, starting from tert-butyl 6α-[1(R)-tert-butyldimethylsilyloxyethyl]-penicillanate-1-oxide; reaction time 6 h; δ (CDCl$_3$) 0.06 (6H, s, SiMe$_2$), 0.9 (9H, s, SiBu$^t$), 1.26 (3H, d, J=6 Hz, CH$_3$.CH), 1.48 (9H, s, OBu$^t$), 1.95 (3H, s, =C.CH$_3$), 3.40 (1H, dd, J=2 and 4 Hz, CH.CH.CH), 4.20 (1H, m, CH$_3$.CH.CH), 4.71 (1H, s, N.CH.CO), 5.1 (2H, br s, CH$_2$=C), 5.42 (1H, d, J=2 Hz, CH.CH.S), and 7.2–7.9 ppm (4H, m, Ar);
3(S)-[1(R)-tert-butuyldimethylsilyloxyethyl]-4(R)-benzthiazolyldithio-1-(1-diphenylmethoxycarbonyl-2-methyl-1-prop-2-enyl)-azetidin-2-one, $\gamma_{max}$ (film) 1772 and 1743 cm$^{-1}$; δ (CDCl$_3$) 0.05 (6H, s, SiMe$_2$), 0.80 (9H, s, SiBu$^t$), 1.29 (3H, d, J=6 Hz, CH$_3$.CH), 1.95 (3H, s, =C.CH₃) 3.45 (1H, dd, J=2 and 4 Hz, CH.CH.CH), 4.26 (1H, m, CH₃.CH.CH), 4.95 (1H, s, N.CH.CO), 5.08 (2H, ABq, separation of inner lines 5 Hz, CH₂=C), 5.55 (1H, d, J=2 Hz, CH.CH.S), 6.93 (1H, s, OCHPh₂), and 7.1–8.0 ppm (14H, m, Ar);

3(S)-[1(R)-trichloroethoxycarbonyloxyethyl]-4(R)-benzthiazolyldithio-1-(1-methoxycarbonyl-2-methyl-1-prop-2-enyl)-azetidin-2-one, starting from methyl 6α-[1(R)-trichloroethoxycarbonyloxyethyl]-penicillanate-1-oxide; γ$_{max}$ (CHCl₃) 1775 and 1745 cm$^{-1}$; δ (CDCl₃) 1.48 (3H, d, J=6 Hz, CH₃.CH), 1.91 (3H, s, =C.CH₃), 3.69 (3H, s, OCH₃), 3.70 (1H, dd, CH.CH.CH), 4.68 (s, 2H, OCH₂), 4.76 (1H, s, N.CH.CO), 5.03–5.30 (2H, m, CH₂=C), 5.23 (1H, m, CH₃.CH.CH), 5.32 (1H, d, J=2 Hz, CH.CH.S), and 7.10–7.96 ppm (4H, m, Ar);

and, in a likenise fashion, starting from the corresponding tert-butyl and diphenylmethyl penicillanates, 3(S)-[1(R)-trichloroethoxycarbonyloxyethyl]-4(R)-benzthiazolyldithio-1-(1-tert-butoxycarbonyl-2-methyl-1-prop-2-enyl)-azetidin-2-one;

3(S)-[1(R)-trichloroethoxycarbonyloxyethyl]-4(R)-benzthiazolyldithio-1-(1-diphenylmethoxycarbonyl-2-methyl-1-prop-2-enyl)-azetidin-2-one;

and, starting from methyl 6β-[1(R)-tert-butyldimethylsilyloxyethyl]-penicillanate-1-oxide, 3(R)-[1(R)-tert-butyldimethylsilyloxyethyl]-4(R)-benzthiazolyldithio-1-(1-methoxycarbonyl-2-methyl-1-prop-2-enyl)-azetidin-2-one.

EXAMPLE 8

3(S)-[1(R)-hydroxyethyl]-4(R)-benzthiazolylldithio-1-(1-methoxycarbonyl-2-hydroxy-1-prop-1-enyl)-azetidin-2-one

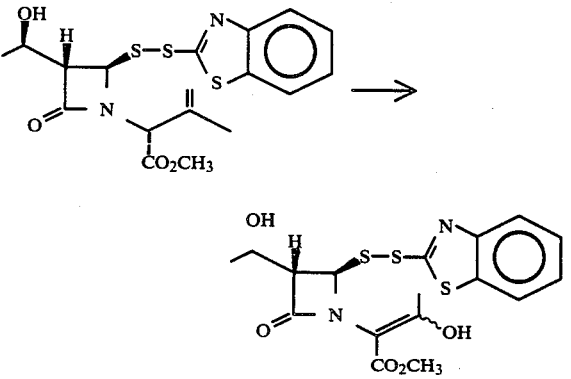

The crude 3(S)-[1(R)-hydroxyethyl]-4(R)-benzthiazolyldithio-1-(1-methoxycarbonyl-2-methyl-1-prop-2-enyl)-azetidin-2-one as obtained in Example 6 was dissolved in dry dichloromethane (300 ml) and treated with a stream of ozone at −70° C. until TLC showed that all the starting material had reacted. The solution was purged with nitrogen and then sodium metabisulphite (10 g) was added at −30° C. The mixture was let rise to room temperature under vigorous stirring, then filtered. The solution was washed with aqueous 4% NaHCO₃, dried over Na₂SO₄ and evaporated. The residue was taken up in ethyl ether, the undissolved matter filtered off and the solution was evaporated to give the crude title product. An aliquot was purified by flash chromatography over silica gel (ethyl acetate-cyclohexane mixture as eluants); δ (CDCl₃) 1.35 (3H, d, J=7 Hz, CH₃.CH), 2.11 (3H, s, CH₃), 2.75 (1H, br s, OH), 3.44 (1H, dd, J=2.0 and 5.0 Hz, CH.CH.CH), 3.79 (3H, s, OCH₃), 4.26 (1H, m, CH₃.CH.CH), 5.29 (1H, d, J=2.0 Hz, CH.CH.S), and 7.25–7.95 ppm (4H, m, Ar).

By using a similar procedure, there was obtained:

3(S)-[1(R)-tert-butyldimethylsilyloxyethyl]-4(R)-benzthiazolyldithio-1-(1-methoxycarbonyl-2-hydroxy-1-prop-1-enyl)-azetidin-2-one, starting from crude 3(S)-[1(R)-tert-butyldimethylsilyloxyethyl]-4(R)-benzthiazolyldithio-1-(1-methoxycarbonyl-2-methyl-1-prop-2-enyl)-azetidin-2-one; γ$_{max}$ (film) 3350, 1770 and 1660 cm$^{-1}$; δ (CDCl₃) 0.05 and 0.07 (6H, each s, SiMe₂), 0.87 (9H, s, SiBuᵗ), 1.27 (3H, d, J=6.5 Hz, CH₃.CH), 2.07 (3H, s, =C.CH₃), 3.33 (1H, dd, J=2.2 and 4.2 Hz, CH.CH.CH), 3.74 (3H, s, OCH₃), 4.26 (1H, m, CH₃.CH.CH), 5.36 (1H, d, J=2.2 Hz, CH.CH.S), 7.2–7.9 (4H, m, Ar), and 12.37 ppm (1H, br s, OH);

3(R)-[1(R)-tert-butyldimethylsilyloxyethyl]-4(R)-benzthiazolyldithio-1-(1-methoxycarbonyl-2-hydroxy-1-prop-1-enyl)-azetidin-2-one, starting from 3(R)-[1(R)-tert-butyldimethylsilyloxyethyl]-4(R)-benzthiazolyldithio-1-(1-methoxycarbonyl-2-methyl-1-prop-2-enyl)-azetidin-2-one; γ$_{max}$ (film) 3200, 1773, 1710, 1665 and 1620 cm$^{-1}$; δ (CDCl₃) 0.20 (6H, s, SiMe₂), 0.94 (9H, s, SiBuᵗ), 1.52 (3H, d, J=6 Hz, CH₃.CH), 2.17 (3H, br s, =C.CH₃), 3.6–3.7 (4H, s+dd, OCH₃ and CH.CH.CH), 4.4 (1H, m, CH₃.CH.CH), 5.25 (1H, d, CH.CH.S), and 7.3–7.9 ppm (4H, m, Ar);

3(S)-[1(R)-hydroxyethyl]-4(R)-benzthiazolyldithio-1-(1-diphenylmethoxycarbonyl-2-hydroxy-1-prop-1-enyl)-azetidin-2-one, starting from crude 3(S)-[1(R)-hydroxyethyl]-4(R)-benzthiazolyldithio-1-(1-diphenylmethoxycarbonyl-2-methyl-1-prop-2-enyl)-azetidin-2-one; γ$_{max}$ (CHCl₃ film) 3400, 1770, 1730 and 1650 cm$^{-1}$;

3(S)-[1(R)-tert-butyldimethylsilyloxyethyl]-4(R)-benzthiazolyldithio-1-(1-diphenylmethoxycarbonyl-2-hydroxy-1-prop-1-enyl)-azetidin-2-one, starting from crude 3(S)-[1(R) tert-butyldimethylsilyloxyethyl]-4(R)-benzthiazolyldithio-1-(1-diphenylmethoxycarbonyl-2-methyl-1-prop-2-enyl)-azetidin-2-one; γ$_{max}$ (CHCl₃ film) 3400, 1775, 1735, 1700 sh, 1655, and 1610 cm$^{-1}$; δ (CDCl₃) 0.06 (6H, s, SiMe₂), 0.82 (9H, s, Buᵗ), 1.26 (3H, d, J=6 Hz, CH₃.CH), 2.08 (3H, s, =C.CH₃), 3.33 (1H, dd, J=2 and 5.5 Hz, CH.CH.CH), 4.18 (1H, m, CH₃.CH.CH), 5.22 (1H, d, J=2 Hz, CH.CH.S), 6.86 (1H, s, OCHPh₂), and 7.2–7.9 ppm (14H, m, Ar);

3(S)-[1(R)-trichloroethoxycarbonyloxyethyl]-4(R)-benzthiazolyldithio-1-(1-methoxycarbonyl-2-hydroxy-1-prop-1-enyl)-azetidin-2-one; δ (CDCl₃) 1.50 (3H, d, J=6 Hz, CH₃.CH), 2.14 (3H, s, =C.CH₃), 3.67 (1H, dd, J=2.2 and 5.5 Hz, CH.CH.CH), 3.82 (3H, s, OCH₃), 4.62 (2H, ABq, J=12 Hz, separation of inner lines 2 Hz, OCH₂), 5.10–5.40 (2H, m, CH₃.CH.CH and CH.CH.S), 7.20–8.00 (4H, m, Ar), and 12.40 ppm (1H, br s, OH);

and in a likewise fashion, starting from the corresponding tert-butyl and diphenylmethylester, 3(S)-[1(R)-trichloroethoxycarbonyloxyethyl]-4(R)-benzthiazolyldithio-1-(1-tert-butoxycarbonyl-2-hydroxy-1-prop-1-enyl)-azetidin-2-one;

3(S)-[1(R)-trichloroethoxycarbonyloxyethyl]-4(R)-benzthiazolyldithio-1-(1-diphenylmethoxycarbonyl-2-hydroxy-1-prop-1-enyl)-azetidin-2-one;

3(S)-[1(R)-tert-butyldimethylsilyloxyethyl]-4(R)-benzthiazolyldithio-1-(1-tert-butoxycarbonyl-2-hydroxy-1-prop-1-enyl)-azetidin-2-one.

EXAMPLE 9

3(S)-[1(R)-hydroxyethyl]-4(R)-benzthiazolyldithio-1-(1-methoxycarbonyl-2-methylsulphonyloxy-1-prop-1-enyl)-azetidin-2-one

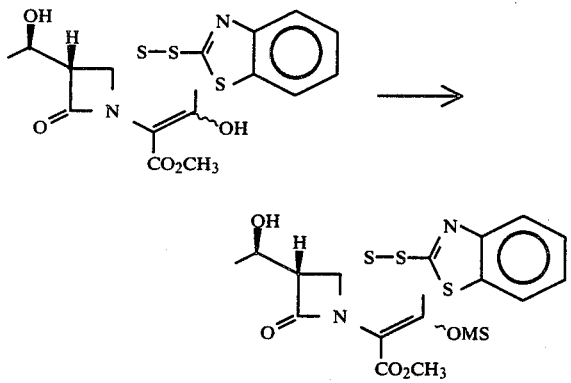

A solution of 3(S)-[1(R)-hydroxyethyl]-4(R)-benzthiazolyldithio-1-(1-methoxycarbonyl-2-hydroxy-1-prop-1-enyl)-azetidin-2-one (130 mg, 0.3 mmol) in anhydrous dichloromethane (8 ml) was sequentially treated at −40° C. with triethylamine (0.043 ml, 0.3 mmol) and methanesulphonyl chloride (0.024 ml, 0.31 mmol). The reaction was quenched after 5 minutes with cold aqueous 2% NaHCO$_3$. Removal of the solvent from the organic layer gave the crude title product (quantitative yield), which was used as such for the next step.

By following the same experimental procedure, there was obtained:

3(S)-[1(R)-tert-butyldimethylsilyloxyethyl]-4(R)-benzthiazolildithio-1-(1-methoxycarbonyl-2-methylsulphonyloxy-1-prop-1-enyl)-azetidin-2-one, starting from 3(S)-[1(R)-tert-butyldimethylsilyloxyethyl]-4(R)-benzthiazolyldithio-1-(1-methoxycarbonyl-2-hydroxy-1-prop-1-enyl)-azetindin-2-one; an aliquot of this product was purified by flash chromatography (silica gel; ethyl acetate-cyclohexane mixtures as eluant) to afford the pure title compound as a 1:1 mixture of E and Z isomers; $\gamma_{max}$ (film) 1885, 1730, 1363, and 1165 cm$^{-1}$; δ (CDCl$_3$) 0.05 and 0.10 (each 3H, s, SiMe$_2$), 0.88 (9H, s, SiBu$^t$), 1.29 (3H, d, J=6.5 Hz, CH$_3$.CH), 2.20 and 2.53 (3H, each s, =C.CH$_3$), 3.18 and 3.29 (3H, each s, SO$_2$CH$_3$), 3.42 (1H, m, CH.CH.CH), 3.71 and 3.78 (3H, each s, OCH$_3$), 4.30 (1H, m, CH$_3$.CH.CH), 5.59 and 5.64 (1H, each d, J=2 Hz, CH.CH.S), and 7.12-7.96 ppm (4H, m, Ar).

When tetrahydrofuran was used instead of dichloromethane as a solvent, the formation of the undesired E isomer was almost suppressied, and the pure Z isomer thus collected; δ (CDCl$_3$) 0.05 (6H, s, SiMe$_2$), 0.88 (9H, s, SiBu$^t$), 1.29 (3H, d, J=6.5 Hz, CH$_3$.OH), 2.53 (3H, s, =C.CH$_3$), 3.29 (3H, s, SO$_2$CH$_3$), 3.42 (1H, dd, J=2 and 5 Hz, CH.CH.CH), 3.71 (3H, s, OCH$_3$), 4.30 (1H, m, CH$_3$.CH.CH), 5.59 (1H, d, J=2 Hz, CH.CH.S), and 7.12-7.95 ppm (4H, m, Ar).

By following this last procedure (tetrahydrofuran as a solvent in the mesylation step), there were obtained:

3(R)-[1(R)-tert-butyldimethylsilyloxyethyl]-4(R)-benzthiazolyldithio-1-[1-methoxycarbonyl-2-methylsulphonyloxy-1-prop-1-(Z)-enyl]-azetidin-2-one, starting from 3(R)-[1(R)-tert-butyldimethylsilyloxyethyl]-4(R)-benzthiazolyldithio-1-(1-methoxycarbonyl-2-hydroxy-1-prop-1-enyl)-azetidin-2-one; $\gamma_{max}$ (CHCl$_3$ film) 1775, 1735, 1365 and 1165 cm$^{-1}$; δ (CDCl$_3$) 0.18 (6H, s, SiMe$_2$), 0.88 (9H, s, SiBu$^t$), 1.42 (3H, d, J=6.5 Hz, CH$_3$.CH), 2.33 (3H, s, =C.CH$_3$), 3.05 (3H, s, SO$_2$CH$_3$), 3.45 (3H, s, OCH$_3$), 3.62 (1H, dd, CH.CH.CH), 4.3 (1H, m, CH$_3$.CH.CH), 5.40 (1H, d, J=5 Hz, CH.CH.S), and 7.15-7.85 ppm (4H, m, Ar);

3(S)-[1(R)-hydroxyethyl]-4(R)-benzthiazolyldithio-1-[1-diphenylmethoxycarbonyl-2-methylsulphonyloxy-1-prop-1-(Z)-enyl]-azetidin-2-one, starting from 3(S)-[1(R)-hydroxyethyl]-4(R)-benzthiazolyldithio-1-(1-diphenylmethoxycarbonyl-2-hydroxy-1-prop-1-enyl)-azetidin-2-one; $\gamma_{max}$ (film 3400, 1775, 1730, 1365 and 1170 cm$^{-1}$; δ (CDCl$_3$) 1.22 (3H, d, J=6.5 Hz, CH$_3$.CH), 2.43 (3H, s, =C.CH$_3$), 3.13 (3H, s, SO$_2$CH$_3$), 3.35 (1H, dd, J=2.5 and 4 Hz, CH.CH.CH), 4.1 (1H, m, CH$_3$.CH.CH), 5.40 (1H, d, J=2.5 Hz, CH.CH.S), 6.85 (1H, s, OCHPh$_2$) and 7.1-7.9 ppm (14H, m, Ar);

3(S)-[1(R)-tert-butyldimethylsilyloxyethyl]-4(R)-benzthiazolyldithio-1-(1-diphenylmethoxycarbonyl-2-(Z)-methylsulphonyloxy-1-prop-1-enyl)-azetidin-2-one, starting from 3(S)-[1(R)-tert-butyldimethylsilyloxyethyl]-4(R)-benzthiazolyldithio-1-(1-diphenylmethoxycarbonyl-2-hydroxy-1-prop-1-enyl)-azetidin-2-one; $\gamma_{max}$ (CHCl$_3$ film) 1775, 1725, 1370, and 1175 cm$^{-1}$; δ (CDCl$_3$) 0.1 (6H, s, SiMe$_2$), 0.9 (9H, s, SiBu$^t$), 1.28 (3H, d, J=6 Hz, CH$_3$.CH), 2.5 (3H, s, =C.CH$_3$), 3.25 (3H, s, SO$_2$CH$_3$), 3.35 (1H, dd, J=2.5 and 5 Hz, CH.CH.CH), 4.20 (1H, m, CH$_3$.CH.CH), 5.50 (1H, d, J=2.5 Hz, CH.CH.S), 6.9 (1H, s, OCHPh$_2$), and 7.1-7.9 ppm (14H, m, Ar);

3(S)-[1(R)-tert-butyldimethylsilyloxyethyl]-4(R)-benzthiazolyldithio-1-(1-tert-butoxycarbonyl-2-(Z)-methylsulphonyloxy-1-prop-1-enyl)-azetidin-2-one, starting from 3(S)-[1(R)-tert-butyldimethylsilyloxyethyl]-4(R)-benzthiazolyldithio-1-(1-tert-butoxycarbonyl-2-hydroxy-1-prop-1-enyl)-azetidin-2-one; $\gamma_{max}$ (film) 1773, 1710, 1370 and 1165 cm$^{-1}$; δ (CDCl$_3$) 0.06 (6H, s, SiMe$_2$), 0.87 (9H, s, SiBu$^t$), 1.25 (3H, d, J=6 Hz, CH$_3$.CH), 1.49 (9H, si, OBu$^t$), 2.45 (3H, s, =C.CH$_3$), 3.25 (3H, s, SO$_2$CH$_3$), 3.35 (1H, dd, J=2.5 and 5 Hz), 4.3 (1H, m, CH$_3$.CH.CH), 5.60 (1H, d, J=2.5 Hz, CH.CH.S), and 7.1-7.9 ppm (4H, m, Ar);

3(S)-[1(R)-trichloroethoxycarbonyloxyethyl]-4(R)-benzthiazolyldithio-1-[1-methoxycarbonyl-2-methylsulphonyloxy-1-prop-1(Z)-enyl]-azetidin-2-one, starting from 3(S)-[1(R)-trichloroethoxycarbonyloxyethyl]-4(R)-benzthiazolyldithio-1-(1-methoxycarbonyl-2-hydroxy-1-prop-1-enyl)-azetidin-2-one; $\gamma_{max}$ (CHCl$_3$ film) 1780, 1755 sh, 1730, 1380, 1250 and 1167 cm$^{-1}$; δ (CDCl$_3$) 1.48 (3H, d, J=6 Hz, CH$_3$.CH), 2.52 (3H, s, =C.CH$_3$), 3.25 (3H, s, SO$_2$CH$_3$), 3.72 (4H, s+dd, OCH$_3$ and CH.CH.CH), 4.68 (2H, s, OCH$_2$), 5.2 (1H, m, CH$_3$.CH.CH), 5.47 (1H, d, J=2.5 Hz, CH.CH.S), and 7.1-7.9 ppm (4H, m, Ar);

and likewise, starting from the corresponding tert-butyl and diphenylmethyl esters, there was obtained:

3(S)-[1(R)-trichloroethoxycarbonyloxyethyl]-4(R)-benzthiazolyldithio-1-[1-tert-butoxycarbonyl-2-methylsulphonyloxy-1-prop-1(Z)-enyl]-azetidin-2-one;

3(S)-[1(R)-trichloroethoxycarbonyloxyethyl]-4(R)-benzthiazolyldithio-1-[1-diphenylmethoxycarbonyl- 2-methylsulphonyloxy-1-prop-1(Z)-enyl]-azetidin-2-one.

EXAMPLE 10

3(S)-[1(R)-methylsulphonyloxyethyl]-4(R)-benzthiazolyldithio-1-(1-methoxycarbonyl-2-methylsulphonyloxy-1-prop-1-enyl)-azetidin-2-one

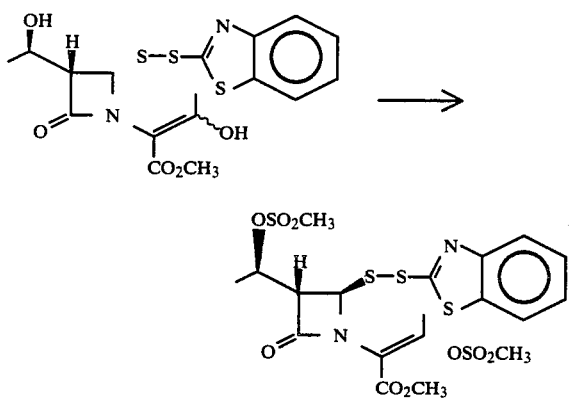

When in the reaction described in Example 8 the starting material was exposed to an excess (2 molar equivalents) of methanesulphonylchloride/triethylamine, the title product was obtained as a foam in quantitative yield as a mixture of E (20%) and Z (80%) isomers; $\gamma_{max}$ (film) 1780, 1730, 1360 and 1170 cm$^{-1}$; δ (CDCl$_3$) 1.58 (3H, d, J=6 Hz, CH$_3$.CH), 2.22 and 2.56 (3H, each s, =C.CH$_3$ of E and Z isomers), 3.00 (3H, s, CH$_3$SO$_2$ on the hydroxyethyl chain), 3.20 (1H, dd, J=2.2 and 4.5 Hz, CH.CH.CH), 3.28 (3H, s, CH$_3$SO$_2$ on the crotonic appendage), 3.76 (3H, s, OCH$_3$), 5.11 (1H, m, CH$_3$.CH.CH), 5.52 (1H, d, J=2.2 Hz, CH.CH.S), and 7.30-7.95 ppm (4H, m, Ar).

By following the same procedure, but using THF as a solvent, 3(S)-[1(R)-methylsulphonyloxyethyl]-4(R)-benzthiazolyldithio-1-[1-diphenylmethoxycarbonyl-2-methylsulphonyloxy-1-prop-1-(Z)-enyl]-azetidin-2-one was prepared and displayed the following spectral data; $\gamma_{max}$ (film) 1777, 1728, 1360 and 1170 cm$^{-1}$; δ (CDCl$_3$) 1.50 (3H, d, J=6 Hz, CH$_3$.CH), 2.52 (3H, s, =C.CH$_3$), 2.9 (3H, s, CH$_3$SO$_2$ on the hydroxyethyl chain), 3.23 (3H, s, CH$_3$SO$_2$ on the crotonic appendage), 3.62 (1H, dd, J=2.5 and 5.5 Hz, CH.CH.CH), 5.05 (1H, m, CH$_3$.CH.CH), 5.45 (1H, d, J=2.5 Hz, CH.CH.S), 6.95 (1H, s, OCHPh$_2$), and 7.10-7.95 ppm (14H, m, Ar).

EXAMPLE 11

3(S)-[1(R)-tert-butyldimethylsilyloxyethyl]-4(R)-benzthiazolyldithio-1-(1-methoxycarbonyl-2-trifluoromethylsulphonyloxy-1-prop-1-enyl)-azetidin-2-one

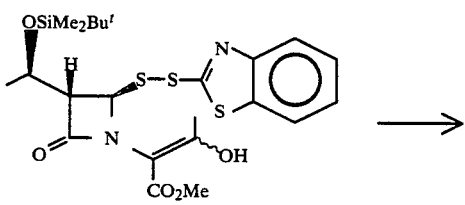

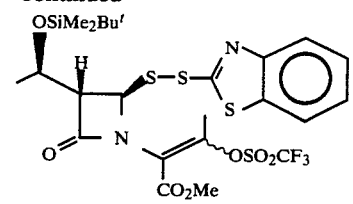

Crude 3(S)-[1(R)-tert-butyldimethylsilyloxyethyl]-4(R)-benzthiazolyldithio-1-(1-methoxycarbonyl-2-hydroxy-1-prop-1-enyl)-azetidin-2-one (300 mg) in THF (5 ml) at −40° C. was sequentially treated with triethylamine (170 ul) and trifluoromethansulphonic anhydride (180 ul). Work-up and chromatography gave the two separate geometrical isomers of the title product, as foams: E isomer: $\gamma_{max}$ (CHCl$_3$) 1778, 1730, 1420, 1215, and 1135 cm$^{-1}$; δ (CDCl$_3$) 0.08 (6H, s, SiMe$_2$), 0.86 (9H, s, SiBu$^t$), 1.26 (3H, d, J=6 Hz, CH$_3$.CH), 2.05 (3H, s, =C.CH$_3$), 3.46 (1H, dd, 2.2 and 4 Hz, CH.CH.CH), 3.81 (3H, s, OCH$_3$), 4.28 (1H, m, CH$_3$.CH.CH), 5.76 (1H, d, J=2.2 Hz, CH.CH.S), and 7.25-7.90 (4H, m, Ar); Z isomer (inter alia) δ (CDCl$_3$) 2.45 (3H, s, =C.CH$_3$), 3.40 (1H, dd, J=2 and 4 Hz, CH.CH.CH), 3.64 (3H, s, OCH$_3$), 4.30 (1H, m, CH$_3$.CH.CH), and 5.65 ppm (1H, d, J=2 Hz, CH.CH.S).

EXAMPLE 12

Methyl(7S,6R)-7-[1(R)-tert-butyldimethylsilyloxyethyl]-3-methyl-2-thiacephem-4-carboxylate

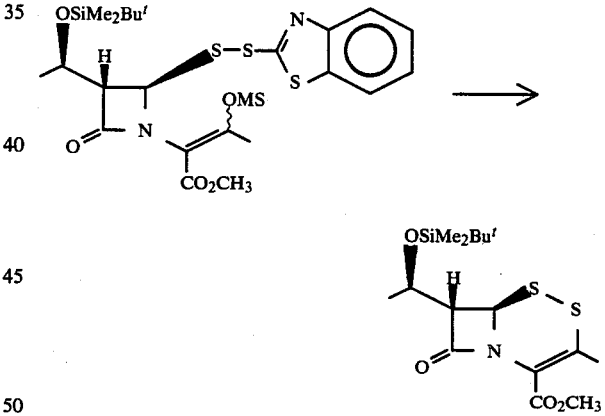

A solution of triethylamine (0.5 ml) in dichloromethane (10 ml) was saturated at −50° C. with hydrogen sulphide. After purging with nitrogen, 0.34 cc. of this solution was added to a cold (−50° C.) solution of 3(S)-[1(R)-tert-butyldimethylsilyloxyethyl]-4(R)-benzthiazolyldithio-1-(1-methoxycarbonyl-2-methylsulphonyloxy-1-prop-1-enyl)-azetidin-2-one (75 mg, 0.121 mmol).

The mixture was allowed to warm up to room temperature and then washed with water, dried (Na$_2$SO$_4$) and evaporated. Separation of the new compound from the formed 2-mercaptobenzthiazole and minor impurities was achieved by silica gel chromatography (ethyl acetate-cyclohexane as eluants), thus obtaining the title compound as white crystals (19 mg, 20%), mp 85°-87° C., $\lambda_{max}$ (EtOH) 223 (68 =4,773), 277 (6,335), and 326 (2,922) nm, $\gamma_{max}$ (CHCl$_3$ film) 1785 and 1730 cm$^{-1}$; δ (CDCl$_3$) 0.08 (6H, s, SiMe$_2$), 0.88 (9H, s, SiBu$^t$), 1.25 (3H, d, J=6 Hz, CH$_3$.CH), 2.22 (3H, s, CH$_3$), 3.07 (1H, dd, J=2.2 and 3.5 Hz, CH.CH.CH), 3.8 (3H, s, OMe), 4.36 (1H, m, CH$_3$.CH.CH), and 4.62 ppm (1H, d, J=2.2 Hz, CH.CH.S). Found: C, 49.08; H, 6.96; N, 3.52; S, 15.16. C$_{16}$H$_{27}$NO$_4$SiS$_2$ requires C, 49.32; H, 6.99; N, 3.60; S, 16.46%.

When, instead of H$_2$S/NEt$_3$, a solution of NaSH (0.9 mol equiv.) in DMF was used, and quenching (partition between H$_2$O and EtOAc) followed within 1 minute at 0° C., the isolated yield of the pure title product raised to 40-45%.

When the above process was prepared on the geometrical Z isomer of the starting material, the yield was further enhanced (up to 60-65%). On the contrary, the E isomer afforded only a very low amount of the title product.

By following the same experimental procedure, methyl(7R,6R)-7-[1(R)-tert-butyldimethylsilyloxyethyl]-3-methyl-2-thiacephem-4-carboxylate was obtained starting from 3(R)-[1(R)-tert-butyldimethylsilyloxyethyl]-4(R)-benzthiazolyldithio-1-(1-methoxycarbonyl-2-methylsulphonyloxy-1-prop-1-enyl)-azetidin-2-one; γ$_{max}$ (film) 1785 and 1725 cm$^{-1}$; δ (CD$_3$COCD$_3$) 0.03 and 0.05 (each 3H, s, SiMe$_2$), 0.84 (9H, s, SiBu$^t$), 1.19 (3H, d, 6.5 Hz, CH$_3$.CH), 2.08 (3H, s, CH$_3$), 3.72 (3H, s, OCH$_3$), 4.11 (1H, dd, J=5.5 and 8.0 Hz, CH.CH.CH), 4.20 (1H, m, CH$_3$.CH.CH), and 5.01 ppm (1H, d, J=5.5 Hz, CH.CH.S).

EXAMPLE 13

Methyl(7S,6R)-7-[1(R)-hydroxyethyl]-3-methyl-2-thiacephem-4-carboxylate

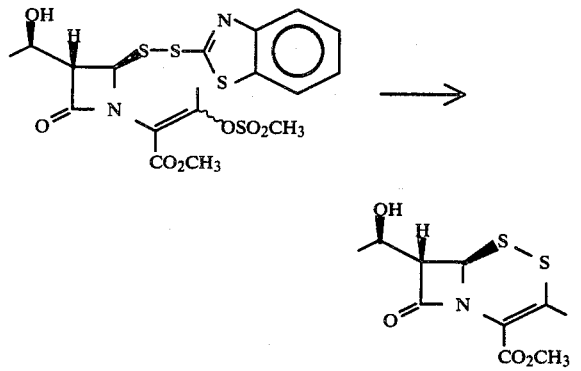

The crude 3(S)-[1(R)-hydroxyethyl]-4(R)-benzthiazolyldithio-1-(1-methoxycarbonyl-2-methylsulphonyloxy-1-prop-1-enyl)-azetidin-2-one (145 mg, 0.287 mmol), as obtained in Example 9, was dissolved in anhydrous dimethylformamide (2 ml) and treated at +20° C. with a freshly prepared solution of NaHS (16 mg, 0.287 mmol) in the same solvent (1.6 ml). The mixture was stirred for 2 minutes and then partitioned between ethyl acetate and water.

After repeated washings with water, the solvent was removed leaving a residue which was purified by pressure chromatography on silica gel (ethyl acetate-cyclohexane as eluants) to give the pure title product in 45% yield as a white powder; γ$_{max}$ (nujol) 3400, 1770 and 1720 cm$^{-1}$; δ (CDCl$_3$) 1.37 (3H, d, J=7 Hz, CH$_3$.CH), 2.22 (3H, s, CH$_3$), 2.40 (1H, br s, OH), 3.12 (1H, dd, J=2.0 and 4.5 Hz, CH.CH.CH), 3.86 (3H, s, OCH$_3$), 4.35 (1H, m, CH$_3$.CH.CH), and 4.65 ppm (1H, d, J=2.0 Hz, CH.CH.S).

By following a similar experimental procedure, there were obtained:

Diphenylmethyl(7S,6R)-7-[1(R)-hydroxyethyl]-3-methyl-2-thiacephem-4-carboxylate, starting from 3(S)-[1(R)-hydroxyethyl]-4(R)-benzthiazolyldithio-1-(1-diphenylmethoxycarbonyl-2-methylsulphonyloxy-1-prop-1-enyl)-azetindin-2-one; λ$_{max}$ (EtOH) 281 (ε=5,900) and 326 (3,670) nm; γ$_{max}$(KBr) 3550-3250, 3080, 3060, 3020, 2960, 2920, 2840, 1775, 1720, 1660 and 1490 cm$^{-1}$; δ (CDCl$_3$) 1.36 (3H, d, J=6.5 Hz), CH$_3$.CH), 2.17 (3H, s, CH$_3$), 3.12 (1H, dd, J=2.0 and 5 Hz, CH.CH.CH), 4.36 (1H, m, CH$_3$.CH.CH), 4.76 (1H, d, J=2.0 Hz, CH.CH.S), 6.97 (1H, s, OCH$_2$Ph), and 7.30 (10H, m, Ar);

Diphenylmethyl(7S,6S)-7-[1(R)-tert-butyldimethylsilyloxyethyl]-3-methyl-2-thiacephem-4-carboxylate, starting from 3(S)-[1(R)-tert-butyldimethylsilyloxyethyl]-4(R)-benzthiazolylditho-1-(1-diphenylmethoxycarbonyl-2-methylsulphonyloxy-1-prop-1-enyl)-azetidin-2-one; δ (CDCl$_3$) 0.06 (6H, s, SiMe$_2$), 0.83 (9H, s, SiBu$^t$), 1.27 (3H, d, J=6.5 Hz, CH$_3$.CH), 2.05 (3H, s, CH$_3$), 3.08 (1H, dd, J=3.0 and 5.0 Hz, CH.CH.CH), 4.32 (1H, m, CH$_3$.CH.CH), 4.60 (1H, d, J=3.0 Hz, CH.CH.S), 7.02 (1H, s, OCHPh$_2$), and 7.30 ppm (10H, s, Ar);

Tert-butyl(7S,6R)-7-[1(R)-tert-butyldimethylsilyloxyethyl]-3-methyl-2-thiacephem-4-carboxylate, starting from 3(S)-[1(R)-tert-butyldimethylsilyloxyethyl]-4(R)-benzthiazolylditho-1-(1-tert-butoxycarbonyl-2-methylsulphonyloxy-1-prop-1-enyl)-azetidin-2-one; λ$_{max}$ (CHCl$_3$) 278 (ε=6,300) and 327 nm (ε=2,560); γ$_{max}$ (CHCl$_3$ film) 1780 and 1720 cm$^{-1}$; δ (CDCl$_3$) 0.12 (6H, s, SiMe$_2$), 0.88 (9H, s, SiBu$^t$), 1.25 (3H, d, J=6 Hz, CH$_3$.CH), 1.52 (9H, s, OBu$^t$), 2.10 (3H, s, CH$_3$), 3.02 (1H, dd, J=2.5 and 5 Hz, CH.CH.CH), 4.28 (1H, m, CH$_3$.CH.CH), and 4.53 ppm (1H, d, J=2.5 Hz, CH.CH.S);

Methyl(7S,6R)-7-[1(R)-methylsulphonyloxyethyl]-3-methyl-2-thiacephem-4-carboxylate, starting from 3(S)-[1(R)-methylsulphonyloxyethyl]-4(R)-benzthiazolyldithio-1-(1-methoxycarbonyl-2-methylsulphonyloxy-1-prop-1-enyl)-azetidin-2-one; γ$_{max}$ 1780, 1725, 1360 and 1175 cm$^{-1}$; δ (CDCl$_3$) 1.60 (3H, d, J=6.5 Hz, CH$_3$.CH), 2.25 (3H, s, CH$_3$), 3.07 (3H, s, CH$_3$SO$_2$), 3.27 (1H, dd, J=2.2 and 5 Hz, CH.CH.CH), 3.83 (3H, s, OCH$_3$), 4.70 (1H, d, J=2.2H, CH.CH.S) and 5.24 ppm (1H, m, CH$_3$.CH.CH).

Diphenylmethyl(7S,6R)-7-[1(R)-methylsulphonyloxyethyl]-3-methyl-2-thiacephem-4-carboxylate, starting from 3(S)-[1-(R)-methylsulphonyloxyethyl]-4(R)-benzthiazolyldithio-1-(1-diphenylmethoxycarbonyl-2-methylsulphonyloxy-1-prop-1-enyl)-azetidin-2-one γ$_{max}$ (CHCl$_3$) 282 (ε=7,080) and 330 (3,966) nm; γ$_{max}$(CHCl$_3$ film) 1778, 1720, 1255 and 1170 cm$^{-1}$; δ (CDCl$_3$) 1.53 (3H, d, J=6 Hz, CH$_3$.CH), 2.10 (3H, s, CH$_3$), 2.71 (3H, s, CH$_3$SO$_2$), 3.22 (1H, dd, J=2.5 and 5.5 Hz, CH.CH.CH), 4.67 (1H, d, J=2.5 Hz, CH.CH.S), 5.05 (1H, m, CH$_3$.CH.CH); 6.90 (1H, s, OCHPh$_2$), and 7.25 (10H, s, Ar);

Methyl(7S,6R)-7-[1(R)-trichloroethoxycarbonyloxyethyl]-3-methyl-2-thiacephem-4-carboxylate, starting from 3(S)-[1(R)-trichloroethoxycarbonyloxyethyl]-4(R)-benzthiazolyldithio-1-(1-methoxycarbonyl-2-methylsulphonyloxy-1-prop-1-enyl)-azetidin-2-one; ν$_{max}$ (film) 1787, 1760 sh, 1725 and 1250 cm$^{-1}$; δ

(CDCl₃) 1.54 (3H, d, J=5.5 Hz, CH₃.CH), 2.23 (3H, s, CH₃) 3.30 (1H, dd, J=2 and 7.5 Hz, CH.CH.CH), 3.84 (3H, s, OCH₃), 4,68 (1H, d, J=2 Hz, CH.CH.S), 4,78 (2H, s, OCH₂), and 5,37 ppm (1H, m, CH₃.CH.CH);

Diphenylmethyl(7S,6R)-7-[1(R)-p-nitrobenzyloxycarbonyloxyethyl]-3-methyl-2-thiacephem-4-carboxylate, starting from (3S)-[1(R)-p-nitrobenzyloxycarbonyloxyethyl].(4R)-benzthiazolyldithio-1-(1-diphenylmethoxycarbonyl-2-methylsulphonyloxy-1-prop-1-enyl)-azetidin-2-one; ν$_{max}$ 1787, 1745, 1720 sh cm⁻¹; δ(CLCl₃) 1.53 (3H, d, CH₃—CH), 2.17 (3H, s, CH₃), 3.28 (1H, dd, J=2 and 6.5 Hz, CH—CH—CH), 4.65 (1H, d, J=2 Hz, CH.CH.S), 5.15 (2H, s, OCH₂), 5.28 (1H, m, CH₂.CH.CH), 6.97 (1H, s, OCHPh₂), 7.2–7.5 (12H, m, Ar) and 8.17 ppm (2H, d, J=9 Hz, Ar); and, likewise, there were obtained:

tert-butyl(7S,6R)-7-[1(R)-trichloroethoxycarbonyloxyethil]-3-methyl-2-thiacephem-4-carboxylate;

diphenylmethyl(7S,6R)-7-[1(R)-trichloroethoxycarbonyloxyethyl]-3-methyl-2-thiacephem-4-carboxylate;

trichloroethyl(7S,6R)-7-[1(R)-trichloroethoxycarbonyloxyethyl]-3-methyl-2-thiacephem-4-carboxylate;

trichloroethyl(7S,6R)-7-[1(R)-tert-butyldimethylsilyloxyethyl]-3-methyl-2-thiacephem-4-carboxylate;

acetoxymethyl(7S,6R)-7-[1(R)-trichloroethoxycarbonyloxyethyl]-3-methyl-2-thiacephem-4-carboxylate;

acetoxymethyl(7S,6R)-7-[1(R)-tert-butyldimethylsilyloxyethyl]-3-methyl-2-thiacephem-4-carboxylate;

acetoxymethyl(7S,6R)-7-[1(R)-trimethylsilyloxyethyl]-3-methyl-2-thiacephem-carboxylate.

EXAMPLE 14

3(S)-[1(R)-tert-butyldimethylsilyloxyethyl]-4(R)-succinimidothio-1-(1-methoxycarbonyl-2-methyl-1-prop-2-enyl)-azetidin-2-one

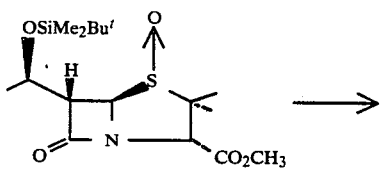

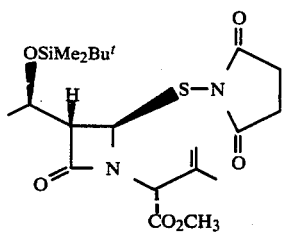

Methyl 6α-[1(R)-tert-butyldimethylsilyloxyethyl]-penicillanate-1-oxide (2.32 g) dissolved in dimethylacetamide (35 ml) was treated with acetic acid (0.15 ml), purged with nitrogen, and heated for 3½ hours at 105° C. in the presence of N-trimethylsilylsuccinimide (5 g). After cooling to room temperature, the reaction mixture was partitioned between ethyl acetate and cold water. Fractionation of the material obtained from the organic layer (silica gel chromatography, ethyl acetate cyclohexane) afforded the title product as a white foam, 1.2 g (43%); γ$_{max}$ (CHCl₃ film) 1770, 1735, 1710 sh, and 1680 cm⁻¹. δ(CDCl₃) 0.08 (6H, s, SiMe₂), 0.87 (9H, s, SiBu'), 1.32 (3H, d, J=6.5 Hz, CH₃.CH), 1.84 (3H, s, =C.CH₃), 2.85 (4H, s, CO.CH₂.CH₂.CO), 3.29 (1H, dd, J=3 and 4.5 Hz, CH.CH.CH), 3.73 (3H, s, OMe), 4.24 (1H, m, CH₃.CH.CH), 4.66 (1H, s, N.CH.CO), 4.85 (1H, d, J=2.5 Hz, CH.CH.S), and 5.00 ppm (2H, br s, CH₂=C).

By following a similar experimental procedure, there were also obtained:

3-(S)-[1(R)-tert-butyldimethylsilyloxyethyl]-4(R)-succinimidothio-1-(1-diphenylmethoxycarbonyl-2-methyl-1-prop-2-enyl)-azetidin-2-one, and 3-(S)-[1(R)-tert-butyldimethylsilyloxyethyl]-4(R)-phthalimidothio-1-(1-diphenylmethoxycarbonyl-2-methyl-1-prop-2-enyl)-azetidin-2-one, both isolated as crude materials and used as such in the following steps.

EXAMPLE 15

3(S)-[1(R)-tert-butyldimethylsilyloxyethyl]-4(R)-phthalimidothio-1-[1-methoxycarbonyl-2-methylsulphonyloxy-1-prop-1-(Z)-enyl]-azetidin-2-one

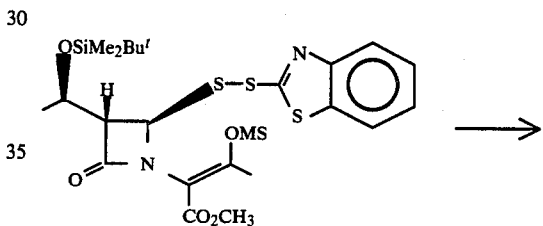

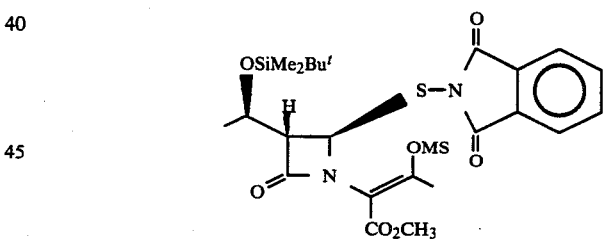

A solution of 3(S)-[1(R)-tert-butyldimethylsilyloxyethyl]-4(R)-benzothiazolyldithio-1-[1-methoxycarbonyl-2-methylsulphonyloxy-1-prop-1-(Z)-enyl]-azetidin-2-one (100 mg) in acetone (9 cc) was treated with AgNO₃ (34 mg), soon followed by an ethanolic slurry of potassium phthalimide (30 mg). After 30 min. stirring at room temperature, the precipitate was collected, partitioned between water and EtOAc, and purified by short silica gel chromatography to afford the title product (55%); γ$_{max}$ (film) 1780, 1745, and 1725 cm⁻¹; δ(CDCl₃) 0.1 (6H, s, SiMe₂), 0.89 (9H, s, Bu'), 1.4 (3H, d, CH₃.CH), 2.2 (3H, s, =C.CH₃), 3.05 (3H, s, SO₂.CH₃), 3.4 (1H, m, CH.CH.CH), 3.6 (3H, s, OCH₃), 4.2 (1H, m, CH₃.CH.CH), 5.45 (1H, d, J=2 Hz, CH.CH.S); and 7.8 ppm (4H, m, Ar).

EXAMPLE 16

3(S)-[1(R)-tert-butyldimethylsilyloxyethyl]-4(R)-succinimidothio-1-(1-methoxycarbonyl-2-hydroxy-1-prop-1-enyl)-azetidin-2-one

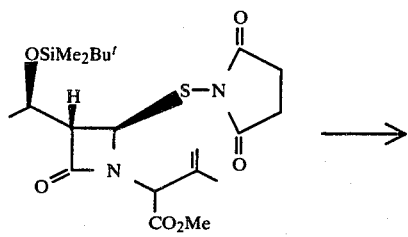

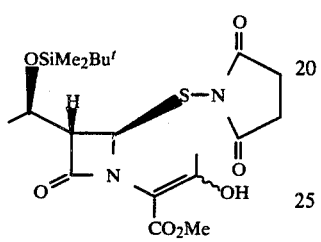

The title product was obtained by ozonolysis of 3(S)-[1(R)-tert-butyldimethylsilyloxyethyl]-4(R)-succinimidothio-1-(1-methoxycarbonyl-2-methyl-1-prop-2-enyl)-azetidin-2-one in dichloromethane according to the procedure described in Example 8, and used as such for further reactions. A sample was characterized as its dimethylketal (MeOH/dry HCl): $\gamma_{max}$ 1770, 1730 and 1715 sh cm$^{-1}$; $\delta$(CDCl$_3$) 0.04 and 0.09 (each 3H, s, SiMe$_2$), 0.90 (9H, s, SiBu$^t$), 1.31 (3H, d, J=5 Hz, CH$_3$.CH), 1.49 (3H, s, CH$_3$), 2.84 (4H, s, COCH$_2$.CH$_2$CO), 3.21 and 3.26 (each 3H, s, ketal OCH$_3$), 3.24 (1H, dd, J=2.5 and 5 Hz), 3.73 (3H, s, ester OCH$_3$), 4.20 (1H, m, CH$_3$.CH.CH), 4.43 (1H, s, N.CH.CO), and 4.94 ppm (1H, d, J=2.5 Hz).

Likewise, 3(S)-[1(R)-tert-butyldimethylsilyloxyethyl]-4(R)-phthalimidothio-1-(1-diphenylmethyoxycarbonyl-2-hydroxy-1-prop-1-enyl)-azetidin-2-one, was obtained starting from 3(S)-[1(R)-tert-butyldimethylsilyloxyethyl]-4(R)-phthalimidothio-1-(1-diphenylmethoxycarbonyl-2-methyl-1-prop-2-enyl)-azetidin-2-one.

EXAMPLE 17

Methyl(7S,6R)-7-[1(R)-tert-butyldimethylsilyloxyethyl]-3-methyl-2-thiacephem-4-carboxylate

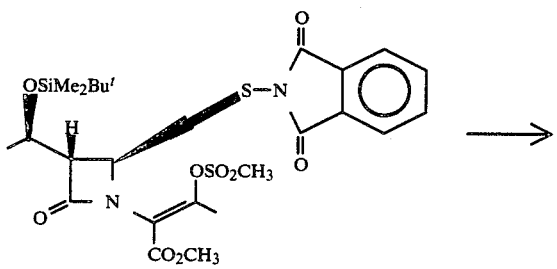

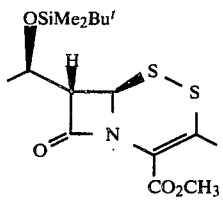

A solution of 3(S)-[1(R)-tert-butyldimethylsilyloxyethyl]-4(R)-phthalimidothio-1-[1-methoxycarbonyl-2-methylsulphonyloxy-1-prop-1-(Z)-enyl]azetidin-2-one (400 mg) in dimethylformamide (4 ml) was treated with finely ground NaSH (50 mg) under vigorous stirring. As soon as the last reagent was dissolved, the reaction was quenched by partition between ethyl ether and water. Work-up gave the title compound, identical with the sample described in Ex. 12.

EXAMPLE 18

Methyl(7S,6R)-7-[1(R)-tert-butyldimethylsilyloxyethyl]-3-methyl-2-thiacephem-4-carboxylate

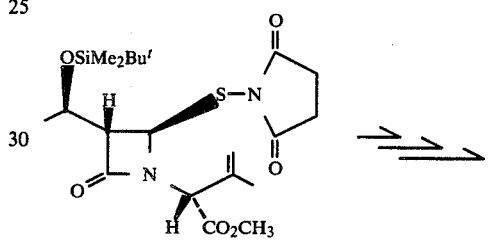

3(S)-[1(R)-tert-butyldimethylsilyloxyethyl]-4(R)-succinimidothio-1-(1-methoxycarbonyl-1-prop-2-enyl)-azetidin-2-one (0.8 g) in dichloromethane was ozonized at −70° C. until tlc showed complete conversion. Excess ozone was purged with nitrogen and dimethylsulphide (1 ml) was added. After 1 hour at room temperature, any volatile material was removed in vacuo and the residue reacted with equimolecular amounts of triethylamine and mesyl chloride (CH$_2$Cl$_2$, −20° to 0° C.) until conversion of the enol into the mesylates was judged complete by tlc. The mixture was concentrated in vacuo and partitioned between ethyl acetate and cold, aqueous NaHCO$_3$. The organic layer was evaporated to afford the crude mixture of E,Z mesylates which without purification was treated with NaHS in DMF according to the procedure described in Example 13. Purification of the resulting product by silica gel chromatography afforded the title compound, identical with the material obtained according to Example 12.

By a similar procedure, Diphenylmethyl(7S,6R)-7-[1(R)-tert-butyldimethylsilyloxyethyl]-3-methyl-2-thiacephem-4-carboxylate was obtained, starting from 3(S)-[1(R)-tert-butyldimethylsilyloxyethyl]-4(R)-phthalimidothio-1-(1-diphenylmethoxycarbonyl-2-methyl-1-prop-2-enyl)- azetidin-2-one, and showed the same spectral properties of the material previously described (Example 13).

EXAMPLE 19

Methyl(7S,6R)-7-[1(R)-tert-butyldimethylsilyloxyethyl]-3-(1-methyl-1,2,3,4-tetrazol-5-yl)-thiomethyl-2-thiacephem-4-carboxylate

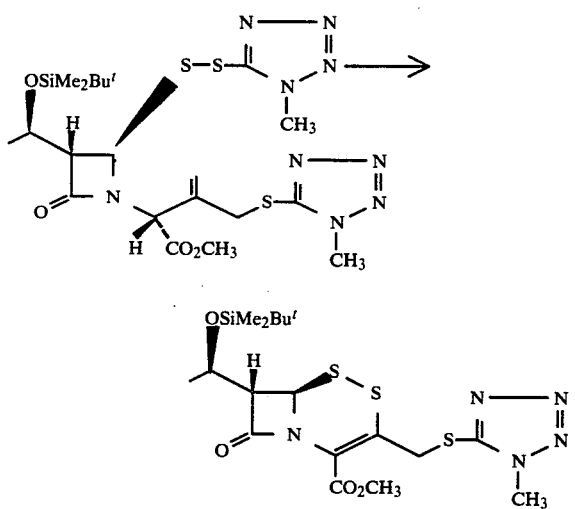

3(S)-[1(R)-tert-butyldimethylsilyloxyethyl]-4(R)-(1-methyl-1,2,3,4-tetrazol-5-yl)-dithio-1-[1-methoxycarbonyl-2-(1-methyl-1,2,3,4-tetrazol-5-yl)-thiomethyl-1-prop-2-enyl]-azetidin-2-one (120 mg) in dichloromethane was subjected to the same reaction sequence reported in Example 17 (ozonolysis, mesylation, reaction with NaHS). The crude product was partitioned between ethyl acetate and aqueous NaHCO3, thus removing the liberated mercaptotetrazole; the organic layer was washed several time with water, evaporated and the residue fractionated by silica gel chromatography to afford the title product, 17 mg (17%); $\gamma_{max}$ (film) 1787, 1725, 1587, 1360 and 1250 cm$^{-1}$; δ (CDCl3) 0.10 (6H, s, SiMe2), 0.89 (9H, s, SiBu$^t$), 1.26 (3H, d, J=6 Hz, CH3—CH), 3.15 (1H, dd, J=2.2 and 3.5 Hz, CH.CH.CH), 3.88 (3H, s, OMe), 3.92 (3H, s, NMe), 4.38 (1H, m, CH3.CH.CH), 4.46 (2H, ABq, J=14 Hz, separation of inner lines 14 Hz) and 4.68 ppm (1H, d, J=2.2 Hz, CH.CH.S).

EXAMPLE 20

3(S)-[1(R)-tert-butyldimethylsilyloxyethyl]-4(R)-phenylsulfphonylthio-1-(1-methoxycarbonyl-2-methyl-1-prop-2-enyl)-azetidin-2-one

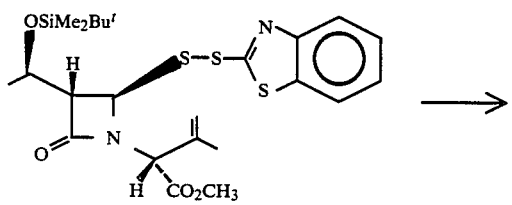

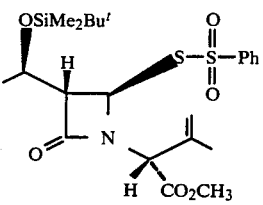

3(S)-[1(R)-tert-butyldimethylsilyloxyethyl]-4(R)-benzthiazolyldithio-1-(1-methoxycarbonyl-2-methyl-1-prop-2-enyl)-azetidin-2-one (2.6 g) in acetone (160 ml) and water (18 ml) was treated under vigorous stirring with silver nitrate (0.98 g), immediately followed by sodium benzenesulphinate (0.79 g) in water (60 ml). After 1 hour at room temperature the white precipitate was filtered off, and the filtrate concentrated in vacuo and then partitioned between water and ethyl acetate. Removal of the solvent from the organic layer left the title product as a yellowish powder (2.43 g, 98%), recrystallizable from cyclohexane (white leaflets, mp 105°–106° C.); ir (KBr) 3080, 3020, 2960, 2930, 2900, 2860, 1770, 1750, 1330 and 1145 cm$^{-1}$; δ (CDCl3) 0.05 (6H, s, SiMe2), 0.98 (12H, s+d, SiBu$^t$ and CH3.CH), 1.84 (3H, s, =C.CH3), 3.22 (1H, dd, J=2 and 2.5 Hz, CH.CH.CH), 3.75 (3H, s, OMe), 4.19 (1H, m, CH3.CH.CH), 4.58 (1H, s, N.CH.CO), 5.00 (2H, m, C=CH2), 5.37 (1H, d, J=2 Hz, CH.CH.S), 7.60 and 7.96 ppm (3 and 2H, each m, Ar). Found: C, 53.69; H, 6.99; N, 2.70; S, 12.42%. C23H35NO6SiS2 requires C, 53.77; H, 6.87; N, 2.74; S, 12.48%.

By following the same procedure, there were also obtained:

3(S)-[1(R)-tert-butyldimethylsilyloxyethyl]-4(R)-phenylsulphonylthio-1-(1-tert-butoxycarbonyl-2-methyl-1-prop-2-enyl)-azetidin-2-one;

3(S)-[1(R)-tert-butyldimethylsilyloxyethyl]-4(R)-phenylsulphonylthio-1-(1-diphenylmethoxycarbonyl-2-methyl-1-prop-2-enyl)-azetidin-2-one;

3(S)-[1(R)-trichloroethoxycarbonyloxyethyl]-4(R)-phenylsulphonylthio-1-(1-methoxycarbonyl-2-methyl-1-prop-2-enyl)-azetidin-2-one;

3(S)-[1(R)-trichloroethoxycarbonyloxyethyl]-4(R)-phenylsulphonylthio-1-(1-trichloroethoxycarbonyl-2-methyl-1-prop-2-enyl)-azetidin-2-one.

EXAMPLE 21

3(S)-[1(R)-tert-butyldimethylsilyloxyethyl]-4(R)-phenylsulphonylthio-1-[1-methoxycarbonyl-2-methyl-sulphonyloxy-1-prop-1(Z)-enyl]-azetidin-2-one

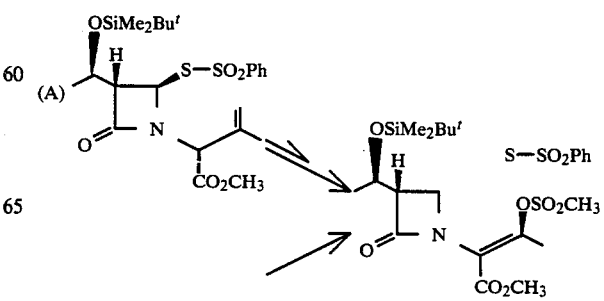

-continued

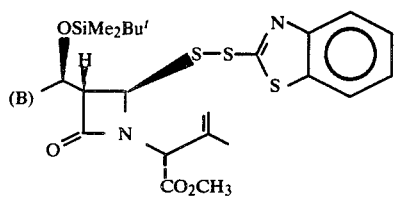

Procedure (A)

The material from Example 20 (1 g) in dry dichloromethane was ozonized at −70° C. After purging with nitrogen, dimethylsulphide (3.5 ml) was added and the mixture stirred for 3 hours at room temperature. After removal of any volatile material in vacuo, the residue was partitioned between ethyl acetate and water. Evaporation of the solvent left the intermediate 3(S)-[1(R)-tert-butyldimethylsilyloxyethyl]-4(R)-phenylsulphonylthio-1-(1-methoxycarbonyl-2-hydroxy-1-prop-1-enyl)-azetidin-2-one; $\gamma_{max}$ 3450, 1778, 1658 and 1620 cm$^{-1}$; δ (CDCl$_3$) 0.08 (6H, s, SiMe$_2$), 0.90 (9H, s, SiBu$^t$), 1.13 (3H, d, J=6 Hz, CH$_3$.CH), 1.90 (3H, s, =C.CH$_3$), 3.12 (1H, dd, J=2.5 and 4 Hz, CH.CH.CH), 3.73 (3H, s, OMe), 4.2 (1H, m, CH$_3$.CH.CH), 5.52 (1H, d, J=2.5 Hz, CH.CH.S), 7.4–8.0 (5H, m, Ar), and 13 ppm (1H, s, OH).

This material was mesylated with triethylamine (272 μl) and mesyl chloride (151 μl) in dry THF (10 ml) according to the general procedure—see Example 10—thus obtaining the title product as a foam, 550 mg after silica gel chromatography; ir (film) 1780, 1730, 1640, 1370 and 1145 cm$^{-1}$; δ (CDCl$_3$) 0.05 (6H, s, SiMe$_2$), 0.80 (9H, s, SiBu$^t$), 0.97 (3H, d, J=6 Hz, CH$_3$.CH), 2.50 (3H, s, =C.CH$_3$), 3.15 (4H, m, SO$_2$CH$_3$ and CH.CH.CH), 3.76 (3H, s, OCH$_3$), 4.13 (1H, m, CH$_3$.CH.CH), 5.7 (1H, d, J=2.8 Hz, CH.CH.S), and 7.6–8.0 ppm (5H, m, Ar).

Procedure (B)

3(S)-[1(R)-tert-butyldimethylsilyloxyethyl]-4(R)-benzthiazolyldithio-1-[1-methoxycarbonyl-2-methylsulphonyloxy-1-prop-1(Z)-enyl]-azetidin-2-one (100 mg) in acetone-water 9:1 (10 ml) was sequentially treated under stirring with silver nitrate (34.3 mg) and an aqueous solution of sodium benzenesulphinate (26.6 mg in 4 ml). After 15 min stirring at room temperature the precipitated silver benzthiazolmercaptide was removed by filtration and the solution partitioned between CH$_2$Cl$_2$ and water. Removal of the solvent left the title product as a syrup (quantitative yield), sharing the same spectral properties with the sample from procedure (A).

According to the same methodology, there were obtained:

3(S)-[1(R)-tert-butyldimethylsilyloxyethyl]-4(R)-phenylsulphonylthio-1-[1-tert-butoxycarbonyl-2-methylsulphonyloxy-1-prop-1(Z)-enyl]-azetidin-2-one;

3(S)-[1(R)-trichloroethoxycarbonyloxyethyl]-4(R)-phenylsulphonylthio-1-[1-trichloroethoxycarbonyl-2-methylsulphonyloxy-1-prop-1(Z)-enyl]-azetidin-2-one.

EXAMPLE 22

Methyl(7S,6R)-7-[1(R)-tert-butyldimethylsilyloxyethyl]-3-methyl-2-thiacephem-4-carboxylate

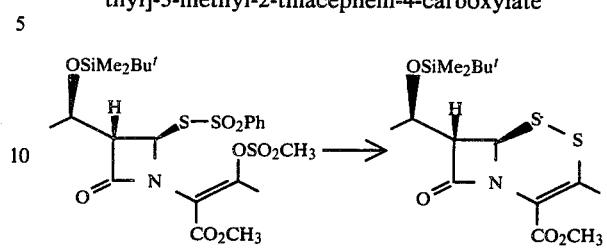

3(S)-[1(R)-tert-butyldimethylsilyloxyethyl]-4(R)-phenylsulphonylthio-1-[1-methoxycarbonyl-2-methylsulphonyloxy-1-prop-1(Z)-enyl]-azetidin-2-one was allowed to react with NaHS in DMF following the procedure described in Example 13 thereby obtaining the title product, identical with the material previously described. This preparation allows for a simpler purification of the product, since the by-product, sodium benzenesulphinate, is soluble in water and does not need chromatographic separation or fractional crystallization to be removed (different from, e.g., mercaptobenzthiazole).

According to the same methodologies, there were obtained:

Tert-butyl(7S,6R)-7-[1(R)-tert-butyldimethylsilyloxyethyl]-3-methyl-2-thiacephem-4-carboxylate;

Trichloroethyl(7S,6R)-7-[1(R)-trichloroethoxycarbonyloxyethyl]-3-methyl-2-thiacephem-4-carboxylate.

EXAMPLE 23

3(S)-[1(R)-trichloroethoxycarbonyloxyethyl]-4(R)-acetyldithio-1-[1-methoxycarbonyl-2-methylsulphonyloxy-1-prop-1(Z)-enyl]azetidin-2-one

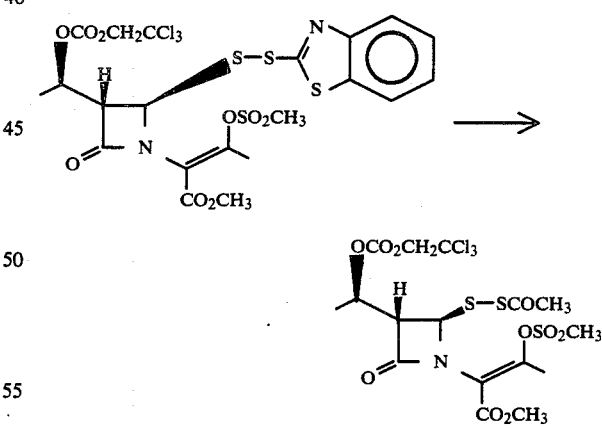

A solution of 3(S)-[1(R)-trichloroethoxycarbonyloxyethyl]-4(R)-benzothiazolyldithio-1-[1-methoxycarbonyl-2-methylsulphonyloxy-1-prop-1(Z)-enyl]azetidin-2-one (340 mg) in THF (5 ml) was treated with thioacetic acid (43 μl). Five minutes later the mixture was evaporated and the crude reaction product freed from 2-mercaptobenzothiazole by chromatography to obtain the pure title compound as a colourless syrup, 280 mg (96%); $\gamma_{max}$ (film) 1775, 1760 sh, 1730 br cm$^{-1}$; δ (CDCl$_3$) 1.50 (3H, d, CH$_3$.CH), 2.48 (3H, s, =C.CH$_3$), 2.62 (3H, s, COCH$_3$), 3.29 (3H, s, SO$_2$CH$_3$), 3.44 (1H, dd, CH.CH.CH), 3.83 (3H, s, OMe), 4.77 (2H, ABq, J=11.5 Hz, separation of inner lines 2 Hz), 5.24 (1H, d, CH.CH.S), 5.25 (1H, m, CH$_3$.CH.CH).

EXAMPLE 24

Methyl(7S,6R)-7-[1(R)-trichloroethoxycarbonyloxyethyl]-3-methyl-2-thiacephem-4-carboxylate

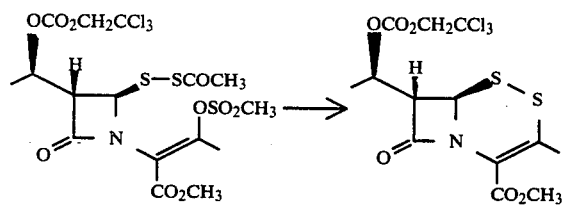

A solution of 3(S)-[1(R)-trichloroethoxycarbonyloxyethyl]-4(R)-acetyldithio-1-[1-methoxycarbonyl-2-methylsulphonyloxy-1-prop-1(Z)-enyl]azetidin-2-one (140 mg) in THF (10 ml) was treated at 0° C. with a solution of tetrabutylammonium hydrogen sulphide (65 mg) in the same solvent.

Work-up and chromatography afforded the title product: $\lambda_{max}$ (EtOH) 280 ($\epsilon$ 4,974) and 327 nm (2,262); $\gamma_{max}$ (film) 1787, 1760 sh, 1725 cm$^{-1}$; $\delta$ (CDCl$_3$) 1.54 (3H, d, CH$_3$.CH), 2.23 (3H, s, CH$_3$), 3.30 (1H, dd, 2 and 7.5 Hz, CH.CH.CH), 3.84 (3H, s, OMe), 4.68 (1H, d, CH.CH.S), 4.78 (2H, s, OCH$_2$CCl$_3$), and 5.3H ppm (1H, m, CH$_3$.CH.CH), followed by some recovered starting material.

EXAMPLE 25

Methyl(7S,6R)-7-[1(R)-tert-butyldimethylsilyloxyethyl]-3-bromomethyl-2-thiacephem-4-carboxylate

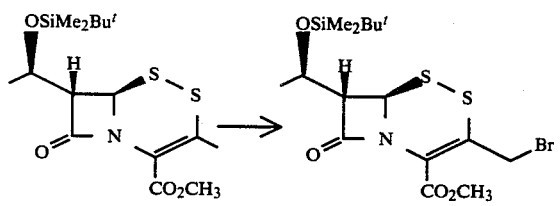

Methyl(7S,6R)-7-[1(R)-tert-butyldimethylsilyloxyethyl]-3-methyl-2-thiacephem-4-carboxylate (0.52 g), propylene oxide (0.95 ml) and N-bromosuccinimide (0.52 g) and azobisisobutyronitrile (0.05 g) in carbon tetrachloride (40 ml) were refluxed for six hours.

The reaction mixture was cooled to room temperature and filtered. The filtrate was evaporated in vacuo and the residue was purified by silica gel column eluting with ethyl acetate-exane mixtures, thus obtaining the title product as a yellowish oil (80%); $\lambda_{max}$ (CHCl$_3$) 282 and 336 nm; $\gamma_{max}$ (CHCl$_3$ film) 1785, 1730 cm$^{-1}$; $\delta$ (CDCl$_3$) 0.10 (6H, s, SiMe$_2$), 0.89 (9H, s, SiBut), 1.28 (3H, d, CH$_3$.CH.OSi), 3.23 (1H, dd, J=2.0 and 3.5 Hz, CH.CH.CH), 3.87 (3H, s, OCH$_3$), 4.65 (2H, center ABq, s.i.l. 4 Hz, J=11.5 Hz, CH$_2$Br), 4.30 (1H, m, CH$_3$.CH.CH), 4.76 (1H, d, J=2.0 Hz, CH.CH.s) ppm Found: C, 41.1; H, 5.64; N, 3.01; S, 13.55; Br, 17.20; C$_{16}$H$_{26}$BrN$_7$O$_4$SiS$_2$ requires C, 41.02; H, 5.59; N, 2.99; S, 13.69; Br, 17.06.

By following a similar procedure, there were obtained:

tert-butyl(7S,6R)-7-[1(R)-tert-butyldimethylsilyloxyethyl]-3-bromomethyl-2-thiacephem-4-carboxylate;

$\nu_{max}$ (CHCl$_3$) 283 and 332 nm; $\nu_{max}$ (film) 1787 and 1720 cm$^{-1}$; $\delta$ (CDCl$_3$) 0.9 (6H, s, SiMe$_2$), 0.9 (9H, s, SiBut), 1.28 (3H, d, CH$_3$.CH), 1.55 (9H, s, OBut), 3.18 (1H, dd, J=2.5 and 4.5 Hz, CH.CH.CH), 4,35 (3H, m, CH$_2$Br and CH$_3$.CH.CH), and 4,71 ppm (1H, d, J=2.5 Hz, CH.CH.S);

p-nitrobenzyl(7S,6R)-7-[1(R)-p-nitrobenzyloxycarbonyloxyethyl]-3-bromomethyl-2-thiacephem-4-carboxylate; $\delta$ (CDCl$_3$) 1.45 (3H, d, CH$_3$.CH), 3.43 (1H, dd, J=2.5 and 6 Hz, CH.CH.CH), 4.45 (2H, ABq, J=12 Hz, CH$_2$Br), 4.80 (1H, d, J=2.5 Hz, CH.CH.S), 5.2, 5.5 (5H, m, two OCH$_2$Ar and CH$_3$.CH.CH); 7.47 and 7.60 (each 2H, d, J=8.5 Hz, Ar), and 8.20 ppm (4H, d, J=8.5 Hz, Ar);

diphenylmethyl(7S,6R)-7-[1(R)-p-nitrobenzyloxycarbonyloxyethyl]-3-bromomethyl-2-thiacephem-4-carboxylate; $\delta$ (CDCl$_3$) 1.45 (3H, d, CH$_3$.CH), 3.32 (1H, dd, J=3 and 6 Hz, CH.CH.CH), 4.18 (2H, ABq, J=11 Hz, CH$_2$Br), 4.70 (1H, d, J=3 Hz, CH.CH.S), 5.20 (2H, s, OCH$_2$Ar), 5.30 (1H, m, CH$_3$.CH.CH), 6.97 (1H, s, OCHPh$_2$), 7.10–7.40 (10H, br s, Ar), 7.45 and 8.15 ppm (each 2H, d, J=9 Hz, Ar);

diphenylmethyl(7S,6R)-7-[1(R)-tert-butyldimethylsilyloxyethyl]-3-bromomethyl-2-thiacephem-4-carboxylate; $\nu_{max}$(film) 1790 and 1730 cm$^{-1}$; $\delta$ (CDCl$_3$) 0.05 (6H, s, SiMe$_2$), 0.8 (9H, s, SiBu$^t$), 1.22 (3H, d, J=6.5 Hz, CH$_3$.CH), 3.10 (1H, dd, J=2.7 and 4.5 Hz, CH.CH.CH), 4.05 (2H, s, CH$_2$Br), 4.2 (1H, m, CH$_3$.CH.CH), 4.63 (1H, d, J=2.7 Hz, CH.CH.S), 6.92 (1H, s, OCHPh$_2$), and 7.05–7.40 ppm (10H, m, Ar); $\lambda_{max}$ (CHCl$_3$) 283 ($\epsilon$=7.867) and 336 nm ($\epsilon$=3.533); and, likewise:

trichloroethyl(7S,6R)-7-[1(R)-tert-butyldimethylsilyloxyethyl]-3-bromomethyl-2-thiacephem-4-carboxylate;

trichloroethyl(7S,6R)-7-[1(R)-trichloroethoxycarbonyloxyethyl]-3-bromomethyl-2-thiacephem-4-carboxylate.

EXAMPLE 26

Methyl(7S,6R)-7-[1(R)-tert-butyldimethylsilyloxyethyl]-3-(1-methyl-1,2,3,4-tetrazol-5-yl)thiomethyl-2-thiacephem-4-carboxylate

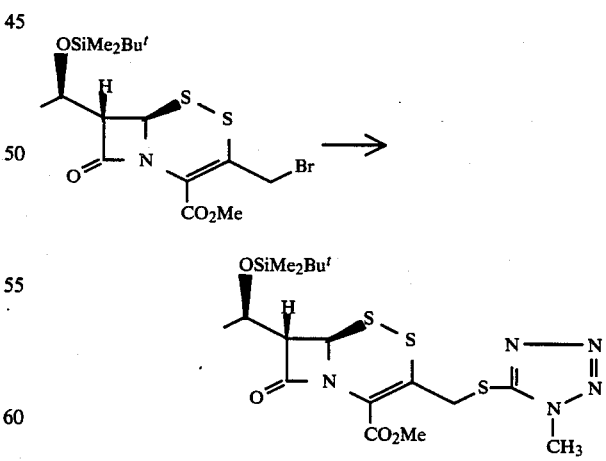

A THF solution of crude methyl(7S,6R)-7-[1(R)-tert-butyldimethylsilyloxyethyl]-3-bromomethyl-2-thiacephem-4-carboxylate was kept overnight in the presence of sodium 1-methyl-1,2,3,4-tetrazol-5-thiolate bihydrate (3 mol equiv.). Work-up and chromatography afforded the title product as an oil in 85% yield; $\lambda_{max}$ (EtOH) 281 and 333 nm; $\gamma_{max}$ (film) 1790 and 1725 cm$^{-1}$; δ (CDCl$_3$) 0.10 (6H, s, SiMe$_2$), 0.89 (9H, s, Bu$^t$), 1.26 (3H, d, CH$_3$.CH), 3.15 (1H, dd, J=2.2 and 3.5 Hz, CH.CH.CH), 3.88 (3H, s, OMe), 3.92 (3H, s, N.CH$_3$), 4.38 (1H, m, CH$_3$.CH.CH), 4.46 (2H, ABq, sep. of inner lines 14 Hz, J=14 Hz), 4.68 (1H, d, CH.CH.S, J=2.2 Hz)

By following a similar procedure, there was obtained: tert-butyl(7S,6R)-7-[1(R)-tert-butyldimethylsilyloxyethyl]-3-(1-methyl-1,2,3,4-tetrazol-5-yl)-thiomethyl-2-thiacephem-4-carboxylate, starting from tert-butyl(7S,6R)-7-[1(R)-tert-butyldimethylsilyloxyethyl]-3-bromomethyl-2-thiacephem-4-carboxylate; diphenylmethyl(7S,6R)-7-[1(R)-tert-butyldimethylsilyloxyethyl]-3-(8-aminotetrazolo[1,5-b]pyridazin-6-yl)thiomethyl-2-thiacephem-4-carboxylate

EXAMPLE 27

(5aR,6S)-6-[1(R)-tert-butyldimethylsilyloxyethyl]-5a,6-dihydro-3H,7H-azeto[2,1-c]furo[3,4-e]-1,2,4-dithiazine-1,7-dione

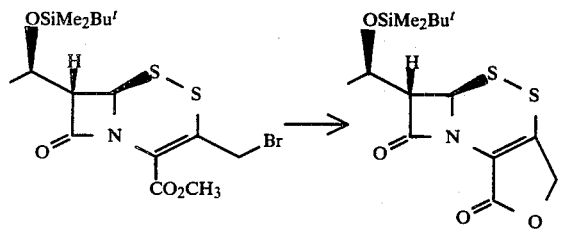

(Procedure A): A solution of methyl(7S,6R)-7-[1(R)-tert-butyldimethylsilyloxyethyl]-3-bromomethyl-2-thiacephem-4-carboxylate (15 mg) in DMSO (2 ml) and water (1.5 ml) was stirred with Cu$_2$O (50 mg) at 50° C. for 2.5 hours. The reaction mixture was partitioned between water and ethyl acetate. Evaporation and chromatography of the organic extracts afforded the title product as a white powder; $\gamma_{max}$ (CHCl$_3$ film) 1800–1760 br cm$^{-1}$; δ (CDCl$_3$) 0.06 (3H, s, SiCH$_3$), 0.11 (3H, s, SiCH$_3$), 0.90 (9H, s, Bu$^t$), 1.33 (3H, d, CH$_3$.CH), 3.33 1H, dd, J=2.5 and 4.5 Hz, CH.CH.CH), 4.44 (1H, m, CH$_3$.CH.CH), 4.62 (1H, d, J=2.5 Hz, CH.CH.S), and 4.98 (2H, s, CH$_2$O)

(Procedure B): The 2-bromomethyl precursor (250 mg) in 2:1 acetone-water (35 ml) was stirred for 15 min at 0° C. with AgClO$_4$ (153 mg). The reaction mixture was partitioned between H$_2$O/EtOAc and the organic layer evaporated to leave a residue. Silica gel chromatography afforded the title product, identical with the sample described above under (A).

EXAMPLE 28 tert-Butyl(7S,6R)-7-[1(R)-tert-butyldimethylsilyloxyethyl]-3-hydroxymethyl-2-thiacephem-4-carboxylate

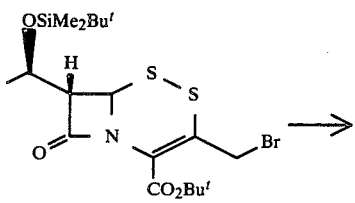

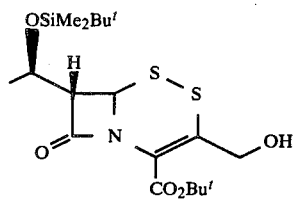

tert-Butyl(7S,6R)-7-[1(R)-tert-butyldimethylsilyloxyethyl]-3-bromomethyl-2-thiacephem-4-carboxylate (300 mg) in 2:1 acetone-water (10 ml) was stirred for 15 min at 0° C. with AgClO$_4$ (150 mg). Removal of the solvent, followed by H$_2$O/EtOAc partition and work-up of the organic layer, gave 250 mg (96%) of the title product; $\lambda_{max}$ (CHCl$_3$) 281 and 335 nm; $\lambda_{max}$ (film) 3450, 1785 and 1712 cm$^{-1}$; δ (CDCl$_3$) 0.1 (6H, s, SiMe$_2$), 0.86 (9H, s, SiBu$^t$), 1.25 (3H, d, CH$_3$CH), 1.50 (9H, s, OBu$^t$), 3.13 (1H, dd, J=2.5 and 4.5 Hz, CH.CH.CH), 4.25 (centre of ABq, J=13 Hz, CH$_2$OH), 4.37 (1H, m, CH$_3$.CH.CH), and 4.60 ppm (1H, d, J=2.5 Hz, CH.CH.S).

EXAMPLE 29 tert-Butyl(7S,6R)-7-[1-(R)-tert-butyldimethylsilyloxyethyl]-3-(N-trichloroacetyl)carbamoyloxymethyl-2-thiacephem-4-carboxylate

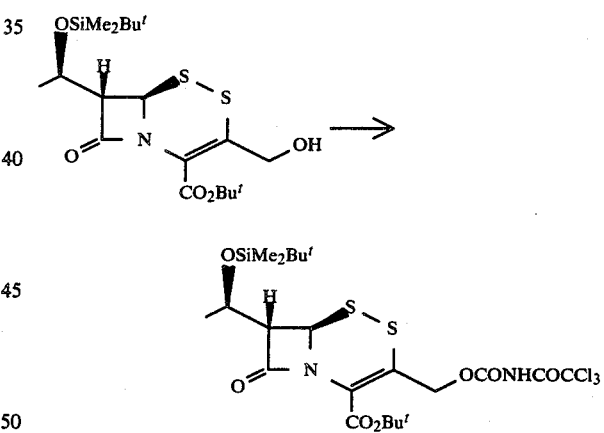

tert-Butyl(7S,6R)-7-[1(R)-tert-butyldimethylsilyloxyethyl]-3-hydroxymethyl-2-thiacephem-4-carboxylate (250 mg) in ethanol-free dichloromethane (2.5 ml) was treated at −40° C. with trichloroacetylisocyanate (80 μl). The mixture was let rise to room temperature and then sequentially washed with aqueous 2% NaHCO$_3$ and brine. Evaporation of the solvent from the organic layer gave the title product in quantitative yield; $\lambda_{max}$ (EtOH) 275 and 329 nm; $\gamma_{max}$ 1795 and 1725 br cm$^{-1}$; δ (CD$_3$CN), 0.1 (6H, s, SiMe$_2$), 0.9 (9H, s, SiBu$^t$), 1.3 (3H, d, CH$_3$.CH) 1.5 (9H, s, OBu$^t$), 3.40 (1H, dd, J=3 and 4 Hz, CH.CH.CH), 4.35 (1H, m, CH$_3$.CH.CH), 4.80 (1H, d, J=3 Hz, CH.CH.S), and 5.0 ppm (centre of ABq, CH$_2$OCO).

EXAMPLE 30 tert-Butyl(7S,6R)-7-[1(R)-tert-butyldimethylsilyloxyethyl]-3-carbamoyloxymethyl-2-thiacephem-4-carboxylate

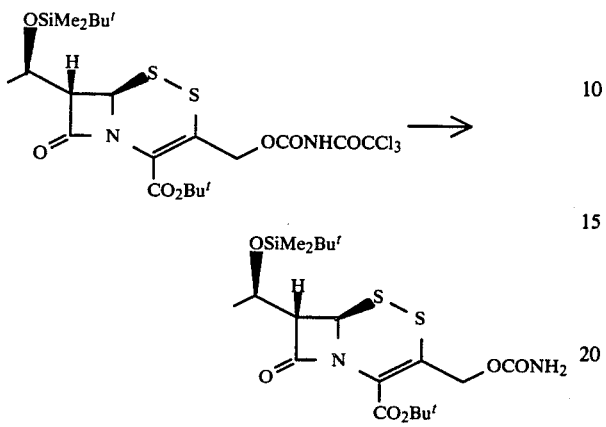

A methanolic solution of tert-butyl(7S,6R)-7-[1(R)-tert-butyldimethylsilyloxyethyl]-3-(N-trichloroacetyl)-carbamoyloxymethyl-2-thiacephem-4-carboxylate was stirred with silica gel for 20 hours. The slurry was then charged onto a silica gel column and the product eluted with ethyl acetate; δ (CDCl$_3$) 0.1 (6H, s, SiMe$_2$), 0.9 (9H, s, SiBu$^t$), 1.35 (3H, d, CH$_3$.CH), 1.60 (9H, s, OBu$^t$), 3.1 (1H, dd, CH.CH.CH), 4.3 (1H, m, CH$_3$.CH.CH) 4.75 (1H, d, J=3 Hz, CH.CH.S), and 5.0 ppm (centre of ABq, OCH$_2$CO).

EXAMPLE 31

Methyl(7S,6R)-7-[1(R)-tert-butyldimethylsilyloxyethyl]-3-nitrooxymethyl-2-thiacephem-4-carboxylate

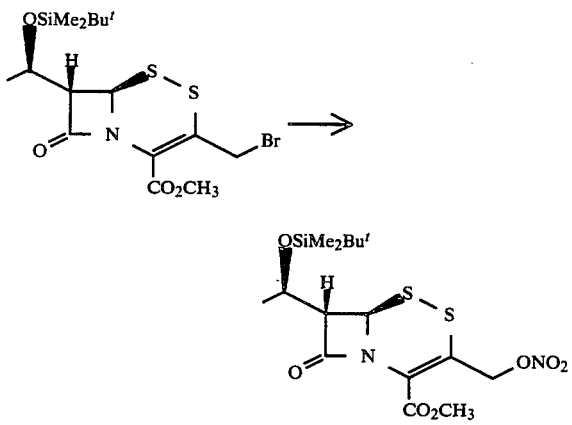

A solution of methyl(7S,6R)-7-[1(R)-tert-butyldimethylsilyloxyethyl]-3-bromomethyl-2-thiacephem-4-carboxylate (200 mg) in acetone (20 ml) was stirred for 20 min in the presence of AgNO$_3$ (100 mg). The filtered reaction mixture was fractionated by silica gel chromatography to obtain the title product, 120 mg; λ$_{max}$ (CHCl$_3$) 280 and 337 nm; γ$_{max}$ (film) 1790, 1730, 1640 and 1280 cm$^{-1}$; δ (CDCl$_3$) 0.08 (6H, s, SiMe$_2$), 0.87 (9H, s, SiBu$^t$), 1.38 (3H, d, CH$_3$.CH), 3.18 (1H, dd, J=2.5 and 5.5 Hz, CH.CH.CH), 3.85 (3H, s, OMe), 4.38 (1H, m, CH$_3$.CH.CH), 4.73 (1H, d, J=2.5 Hz, CH.CH.S), and 5.36 ppm (2H, ABq, J=13.5 Hz, s.i.l.

29.5 Hz, CH$_2$ONO$_2$); further elution then afforded some of the lactone described in Example 27.

EXAMPLE 32

Methyl(7S,6R)-7-[1(R)-tert-butyldimethylsilyloxyethyl]-3-formyloxymethyl-2-thiacephem-4-carboxylate

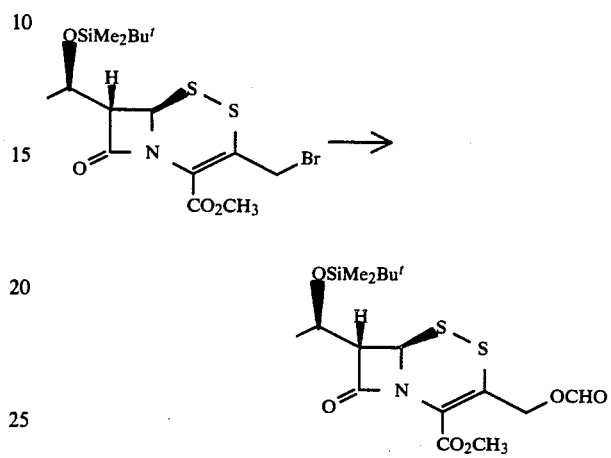

Methyl(7S,6R)-7-[1(R)-tert-butyldimethylsilyloxyethyl]-3-bromomethyl-2-thiacephem-4-carboxylate (200 mg) in CH$_2$Cl$_2$ was treated at daily intervals with tetrabutylammonium formiate (3×600 mg). After 3 days at 5° C. tlc showed 80% conversion in the product (ethyl acetate/light petroleum 1:2). Elution through a short silica gel column gave the title material; δ (CDCl$_3$) 0.1 (6H, s, SiMe$_2$), 0.9 (9H, s, SiBu$^t$), 1.35 (3H, d, CH$_3$.CH), 3.20 (1H, dd, 2.5 and 7 Hz, CH.CH.CH), 3.9 (3H, s, OMe), 4.5 (1H, m, CH$_3$.CH.CH), 4.74 (1H, d, 2.5 Hz, CH.CH.S), 5.13 (center of ABq, CH$_2$O).

In a similar way, starting from the corresponding tert-butyl and diphenylmethyl esters, there were obtained:

tert-butyl(7S,6R)-7-[1(R)-tert-butyldimethylsilyloxyethyl]-3-formyloxymethyl-2-thiacephem-4-carboxylate;

diphenylmethyl(7S,6R)-7-[1(R)-tert-butyldimethylsilyloxyethyl]-3-formyloxymethyl-2-thiacephem-4-carboxylate and, in a likewise fashion, the corresponding acetates were obtained:

methyl(7S,6R)-7-[1(R)-tert-butyldimethylsilyloxyethyl]-3-acetoxymethyl-2-thiacephem-4-carboxylate;

tert-butyl(7S,6R)-7-[1(R)-tert-butyldimethylsilyloxyethyl]-3-acetoxymethyl-2-thiacephem-4-carboxylate;

diphenylmethyl(7S,6R)-7-[1(R)-tert-butyldimethylsilyloxyethyl]-3-acetoxymethyl-2-thiacephem-4-carboxylate;

trichloroethyl(7S,6R)-7-[1(R)-trichloroethoxycarbonyloxyethyl]-3-acetoxymethyl-2-thiacephem-4-carboxylate

EXAMPLE 33

Methyl(7S,6R)-7-[1(R)-hydroxyethyl]-3-methyl-2-thiacephem-4-carboxylate

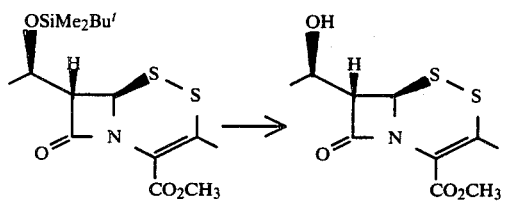

Methyl(7S,6R)-7-[1(R)-tert-butyldimethylsilyloxyethyl]-3-methyl-2-thiacephem-4-carboxylate (0.75 g) was added to a solution of tetrabutylammonium fluoride trihydrate (2.03 g) in acetic acid (1.23 ml) and THF (10 ml).

Work-up after 20 hours gave the title compound (virtually quantitative yield), showing the spectral properties described for the sample obtained in Example 13.

By following a similar experimental procedure, there were obtained:

Methyl(7S,6R)-7-[1(R)-hydroxyethyl]-3-bromomethyl-2-thiacephem-4-carboxylate, starting from methyl(7S,6R)-7-[1(R)-tert-butyldimethylsilyloxyethyl]-3-bromomethyl-2-thiacephem-4-carboxylate; $\gamma_{max}$ (film) 1775, 1730 cm$^{-1}$; $\delta$ (CDCl$_3$) 1.35 (3H, d, CH$_3$.CH), 3.38 (1H, dd, CH.CH.CH), 3.60 (1H, br s, OH), 3.97 (3H, s, OMe), 4.33 (1H, m, CH$_3$.CH.CH), 4.46 (2H, centre of ABq, J=11 Hz, sep. of inner lines 4 Hz, CH$_2$Br), and 4.88 ppm (1H, d, J=2.2 Hz, CH.CH.S);

Methyl(7S,6R)-7-[1(R)-hydroxyethyl]-3-(1-methyl-1,2,3,4-tetrazol-5-yl)thiomethyl-2-thiacephem-4-carboxylate, starting from methyl (7S,6R)-7-[1(R)-tert-butyldimethylsilyloxyethyl]-3-(1-methyl-1,2,3,4-tetrazol-5-yl)thiomethyl-2-thiacephem-4-carboxylate; $\gamma_{max}$ (KBr) 1765 and 1707 cm$^{-1}$; $\delta$ (CD$_3$COCD$_3$) 1.30 (3H, d, CH$_3$.CH), 3.39 (1H, dd, CH.CH.CH), 3.79 (3H, s, NCH$_3$), 3.97 (3H, s, OCH$_3$), 4.0 (1H, m, CH$_3$.CH.CH), 4.38 (2H, centre of ABq, J=16 Hz, separation of inner lines 13 Hz, CH$_2$.S), 4.77 (1H, d, J=2.2 Hz, CH.CH.S) and 5.0 ppm (1H, br s, OH); and, analogously, the corresponding tert-butyl, diphenylmethyl and trichloroethyl esters were also prepared.

EXAMPLE 34

(7S,6R)-7-[1(R)-methylsulphonyloxyethyl]-3-methyl-2-thiacephem-4-carboxylic acid

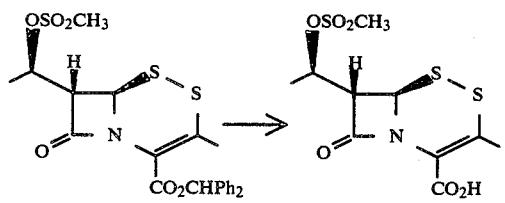

Diphenylmethyl(7S,6R)-7-[1(R)-methylsulphonyloxyethyl]-3-methyl-2-thiacephem-4-carboxylate was dissolved in cold trifluoroacetic acid (0° C., neat). After 15' stirring at the same temperature, carbon tetrachloride was added and the solution thoroughly evaporated under vacuum without external heating. The residue was triturated in CCl$_4$ and collected, thus obtaining the title product; $\lambda_{max}$ (CHCl$_3$) 281 and 326 nm; $\gamma_{max}$ (CHCl$_3$) 3000–2300, 2970, 2930, 2850, 1775, 1710, 1530 and 1170 cm$^{-1}$; $\delta$ (CD$_3$COCD$_3$) 1.58 (3H, d, CH$_3$.CH), 2.23 (3H, s, Me), 3.16 (3H, s, SO$_2$Me), 3.66 (1H, dd, J=2 and 6 Hz, CH.CH.CH), 4.85 (1H, d, J=2 Hz, CH.CH.S), and 5.30 ppm (1H, m, CH$_3$.CH.CH).

The same material was obtained by TFA-hydrolysis of the corresponding t-butyl ester, but prolonging the reaction time to about 1 hour.

Similarly hydrolysis of the t-butyl or diphenylmethyl precursors gave the following products:

(7S,6R)-7-[1(R)-tert-butyldimethylsilyloxyethyl]-3-methyl-2-thiacephem-4-carboxylic acid;

(7S,6R)-7-[1(R)-hydroxyethyl]-3-methyl-2-thiacephem-4-carboxylic acid;

(7S,6R)-7-[1(R)-hydroxyethyl]-3-acetoxymethyl-2-thiacephem-4-carboxylic acid;

(7S,6R)-7-[1(R)-hydroxyethyl]-3-carbamoyloxymethyl-2-thiacephem-4-carboxylic acid;

(7S,6R)-7-[1(R)-hydroxyethyl]-3-(1-methyl-1,2,3,4-tetrazol-5-yl)thiomethyl-2-thiacephem-4-carboxylic acid

EXAMPLE 35

(7S,6R)-7-[1(R)-tert-butyldimethylsilyloxyethyl]-3-methyl-4-methoxycarbonyl-2-thiacephem-1,1-dioxide

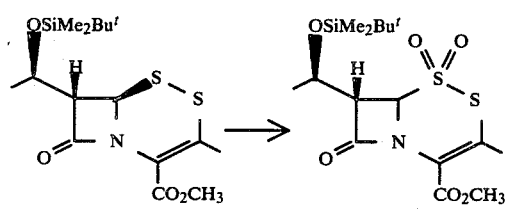

Precedure (a)

A solution of 117 mg of (7S,6R)-7-[1(R)-t-butyldimethylsilyloxyethyl]-3-methyl-4-methoxycarbonyl-2-thiacephem in 5 ml of chloroform was treated with 220 mg of m-chloroperbenzoic acid at 0° C. under stirring. After 30 minutes the reaction mixture was partitioned between dichloromethane and a 2% by weight aqueous sodium bicarbonate solution. The organic layer was dried over anhydrous sodium sulphate and the solvent was evaporated off. The residue was purified by short-path chromatography to afford the title product (89 mg) as a syrup; $\gamma_{max}$ (CH$_2$Cl$_2$ film) 1800, 1735 cm$^{-1}$; $\delta$(CDCl$_3$) 0.10 (6H, s, Me$_2$Si), 0.90 (9H, s, Bu$^t$Si), 1.27 (3H, d, CH$_3$—CH), 2.18 (3H, s, CH$_3$), 3.81–3.83 (1H, dd, +3H, s, CH—CH—CH and OCH$_3$), 4.35 (1H, m, CH$_3$—CH—CH), 5.05 (1H, d, J=2.0 Hz, CH—CH—S) ppm; $\lambda$max (hexane) 276 ($\epsilon$=5.084) and 297 (sh, $\epsilon$=3.745) nm.

Procedure (b)

A solution of 500 mg of (7S,6R)-7-[1(R)-t-butyldimethylsilyloxyethyl]-3-methyl-4-methoxycarbonyl-2-thiacephem in 25 ml of chloroform was treated with 276 mg of 80% m-chloroperbenzoic acid at 20° C. The temperature was allowed to rise to +20° C. within 30 minutes and then, 4% by weight aqueous sodium bicarbonate solution was added.

The organic layer was dried over anhydrous sodium sulphate, and the solvent was evaporated off. The residue was separated by silica gel chromatography to afford in the following order:

the 1,1-dioxide, syrup, 35 mg; NMR and IR data as above;

the 2-oxide, syrup, 60 mg; νmax (CH$_2$Cl$_2$ film) 1795, 1740 cm$^{-1}$; δ (CDCl$_3$) 0.10 (6H, s, Me$_2$Si); 0.90 (9H, s, Bu'Si), 1.24 (3H, d, CH$_3$—CH), 2.35 (3H, S, CH$_3$); 2.85-3.90 (1H, dd, +3H, s, CH—CH—CH and OCH$_3$), 4.35 (1H, m, CH$_3$—CH—CH), 5.27 (1H, d, J=2.5 Hz, CH—CH—S) ppm; λ$_{max}$ (hexane) 276 (ε=5.092) nm;

the 1-oxide, white powder, m.p. 90°-93° C., 330 mg; γmax (CH$_2$Cl$_2$ film) 1790, 1730 cm$^{-1}$; δ 0.10 (6H, s, Me$_2$Si), 0.90 (9H, S, Bu'Si) 1.28 (3H, d, CH$_3$—CH), 2.24 (3H, s, CH$_3$), 3.60 (1H, dd, J=2.0 and 4.0 Hz, CH—CH—CH), 3.87 (3H, s, OCH$_3$), 4.35 (1H, m, CH$_3$—CH—CH), 4.67 (1H, d, J=2.0 Hz CH—CH—S) ppm; λ$_{max}$ (hexane) 273 (ε=4.862), 309 (sh, ε=2,721) nm.

The solution of 300 mg of the 1-oxide in 30 ml of chloroform was stirred for 1 hour at room temperature in the presence of 160 mg of m-chloroperbenzoic acid. The reaction mixture was washed with aqueous sodium bicarbonate solution concentrated and purified by flas-chromatography (silica gel, cyclohexane:ethyl acetate as eluent) thus obtaining a further 280 mg of the title product.

EXAMPLE 36

Methyl(6S,5R)-6-[1(R)-tert-butyldimethylsilyloxyethyl]-2-methylpenem-3-carboxylate

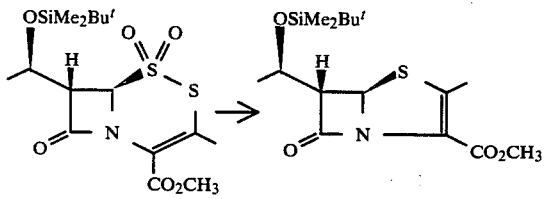

A solution of 300 mg of (7S,6R)-7-[1(R)-t-butyldimethylsilyloxyethyl]-3-methyl-4-methoxycarbonyl-2-thiacephem-1,1-dioxide in chloroform was heated at 50° C. for 5 hours. Removal of the solvent afforded the title compound, free of stereoisomers, in nearly quantitative yield (250 mg); ν$_{max}$ (CHCl$_3$) 1795, 1715 cm$^{-1}$; δ(CDCl$_3$) 0.08 (6H, s, Me$_2$Si), 0.89 (9H, s, Bu'Si), 1.23 (3H, d, CH$_3$—CH; 2.33 (3H, s, CH$_3$), 3.61 (1H, dd, J=1.8 and 5.0 Hz, CH—CH—CH), 3.75 (3, s, OCH$_3$), 4.21 (1H, m, CH$_3$—CH—CH), 5.50 (1H, d, J=1.8 HZ, CH—CH—S); λ$_{max}$ (EtOH) 257, 314 nm.

The above reaction occurred even at room temperature; e.g. after 16 hours standing in chloroform NMR analysis revealed a mixture 1:2 of the title product and the starting material.

EXAMPLE 37

(7S,6R)-7-[1(R)-hydroxyethyl]-3-methyl-4-methoxycarbonyl-2-thiacephem-1,1-dioxide

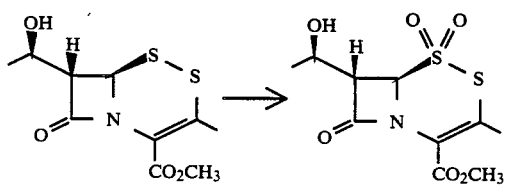

A solution of 40 mg of (7S,6R)-7-[1(R)-hydroxyethyl]-3-methyl-4-methoxycarbonyl-2-ghiacephem in 1 ml of chloroform was stirred at 0° C. for 15 minutes in the presence of 60 mg of m-chloroperbenzoic acid. Partition between ethyl acetate and an acqueous solution of sodium bicarbonate and removal of the solvent left the title compound, which was further purified by silica gel chromatography; δ (CDCl$_3$) 1.36 (3H, d, J=6.4 Hz, CH$_3$—CH), 2.21 (3H, s, CH$_3$), 3.80-3.88 (4H, m, CH—CH—CH and OCH$_3$), 4.40 (1H, m, CH$_3$—CH—CH), 5.08 (1H, d, J=1.6 Hz, CH—CH—S).

EXAMPLE 38

Methyl(6S,5R)-6-[1(R)-hydroxyethyl]-2-methylpenem-3-carboxylate

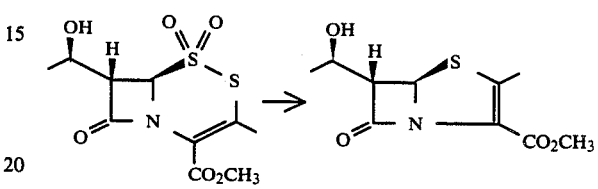

When a solution of the compound prepared in Example 37 in an inert solvent (e.g. chloroform or benzene) was allowed to stand for a few days, or briefly heated at 50°-80° C., the title compound was formed, free of diastereomers, in virtually quantitative yield. δ (CDCl$_3$) 1.34 (3H, d, J=6.4 Hz, CH$_3$—CH) 2.35 (3H, s, CH$_3$), 3.68 (1H, dd, J=6.6 and 1.5 Hz, CH—CH—CH), 3.80 (3H, s, OCH$_3$), 4.40 (1H, m, CH$_3$—CH—CH), 5.56 (1H, d, J=1.5 Hz, CH—CH—S).

EXAMPLE 39

Methyl(6S,5R)-6-[1(R)-tert-butyldimethylsilyloxyethyl]-2-(1-methyl-1,2,3,4-tetrazol-5-yl)thiomethyl-penem-3-carboxylate

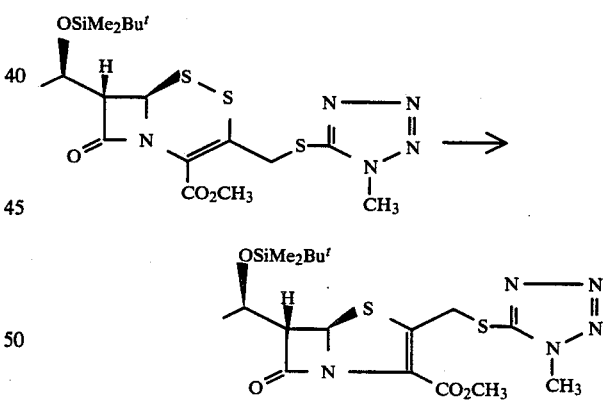

A solution of methyl(7S,6R)-7-[1(R)-tert-butyldimethylsilyloxyethyl]-3-(1-methyl-1,2,3,4-tetrazol-5-yl)thiomethyl-2-thiacephem-4-carboxylate in chloroform was stirred at 0° C. with m-chloroperbenzoic acid (2.5 molar equivalent) for 30 minutes, and then washed with aqueous NaHCO$_3$. The dried organic layer was refluxed for a few hours (t.l.c. monitoring).

Evaporation of the solvent and silica gel chromatography afforded the title product; δ(CDCl$_3$) 0.07 (6H, s, SiMe$_2$), 0.82 (9H, s, SiBu'), 1.20 (3H, d, CH$_3$—CH), 3.68 (1H, dd, 1.8 and 4 Hz, CH.CH.CH), 3.80 (3H, s, N—Me), 3.81 (3H, s, OMe), 4.22 (1H, m, CH$_3$—CH—CH), 4.69 (2H, centre of ABq, J=14 Hz, separation of inner lines 11.5 Hz, CH$_2$S), and 5.54 ppm (1H, d, J=1.8 Hz, CH—CH—S).

EXAMPLE 40 p-Nitrobenzyl(7S,6R)-7-[1(R)-p-nitrobenzyloxycarbonyloxyethyl]-3-methyl-2-thiacephem-4-carboxylate

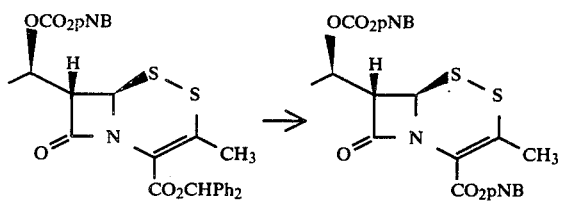

A solution of diphenylmethyl (7S,6R)-7-[1(R)-p-nitrobenzyloxycarbonyloxyethyl]-3-methyl-2-thiacephem-4-carboxylate (200 mg) in dichloromethane (25 ml) was treated for 30 min at 0° C. with trifluoroacetic acid (0.4 ml). Evaporation under vacuum in the cold left the ·crude 2-thiacephem-4-carboxylic acid, which was dissolved in acetonitrile-dimethylformamide (2:1, 10 ml) and treated with triethylamine (0.050 ml) and p-nitrobenzylbromide (100 mg). After 1 hour at 25° C., the mixture was partitioned between ethyl acetate and aq. NaHCO$_3$.

The dried (MgSO$_4$) organic layer was concentrated and the residue passed through a short column of SiO$_2$ (ethyl acetate—light petrol as eluants) to afford the pure title product, 150 mg (79%); δ(CDCl$_3$) 1.45 (3H, d, CH$_3$.CH), 3.43 (1H, dd, J=2.5 and 6 Hz, CH—CH—CH), 4.45 (2H, ABq, J=12 Hz, CH$_2$Br), 4.80 (1H, d, J=2.5 Hz, CH—CH—S), 5.2-5.5 (5H, m), 7.47 and 7.60 (each 2H, d, Ar), and 8.20 ppm (4H, d, Ar).

EXAMPLE 41

(7S,6R)-7-[1(R)-tert-butyldimethylsilyloxyethyl]-4-diphenylmethoxycarbonyl-2-thiacephem-3-(pyridinium)methyl bromide

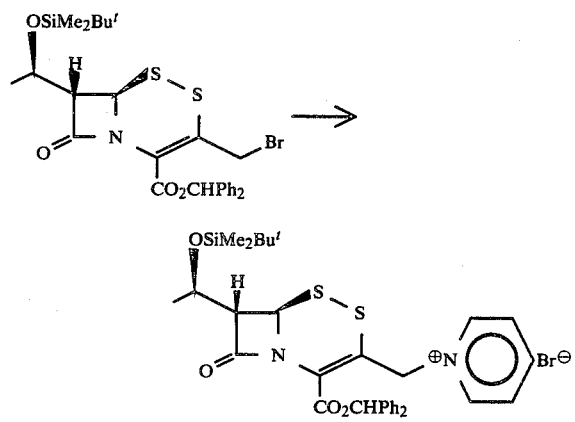

A solution of diphenylmethyl (7S,6R)-7-[1(R)-tert-butyldimethylsilyloxyethyl]-3-bromomethyl-2-thiacephem-4-carboxilate (310 mg) in dry acetone (15 ml) was treated with pyridine (0.4 ml). After 20 hours at room temperature the solvent was distilled off and the residue purified by silica gel chromatography. The product-containing fractions (eluted with CH$_2$Cl$_2$—HOAc—MeOH 70:15:15) were collected and freed from the solvents to leave the title compound as a syrup; ν$_{max}$ (CHCl$_3$ film) 1790, 1715 cm$^{-1}$; δ(CDCl$_3$) (inter alia) 1.32 (3H, d, J=6.5 Hz), 3.33 (1H, dd), 4.45 (1H, m), 5.0 (1H, d, J<2 Hz), 7.11 (1H, s); ν$_{max}$(CHCl$_3$) 283 and 337 nm (ε=4.060). In a likewise manner, and starting from p-nitrobenzyl(7S,6R)-7-[1(R)-p-nitrobenzyloxycarbonyloxyethyl]-3-bromomethyl-2-thiacephem-4-carboxylate, there was obtained:

(7S,6R)-7-[1(R)-p-nitrobenzyloxycarbonyloxyethyl]-4-p-nitrobenzyloxycarbonyl-2-thiacephem-3-(pyridinium)methyl bromide.

EXAMPLE 42

(7S,6R)-7-[1(R)-tert-butyldimethylsilyloxyethyl]-4-carboxy-2-thiacephem-3-(pyridinium)methyl trifluoroacetate

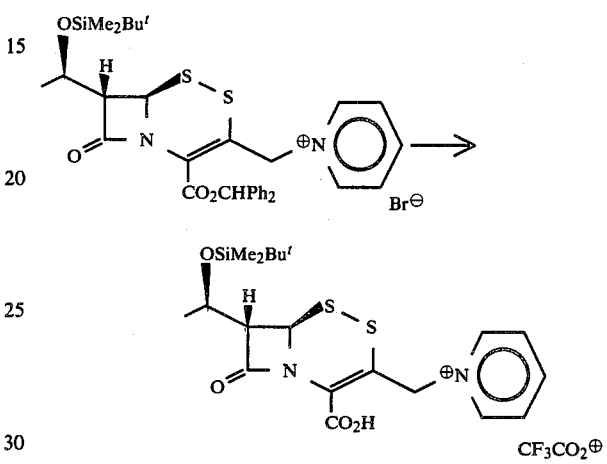

A solution of the diphenylmethyl ester (obtained in Example 41) in dichloromethane (10 ml) was treated with trifluoroacetic acid (2 ml) at 0° C. for 15 min.

After evaporation in vacuo, the residue was taken up in a small amount of chloroform. Ethyl ether was added under stirring and then decanted off, to leave the crude title product; ν$_{max}$ (CHCl$_3$ film) 3420, 1785, 1715 and 1635 br cm$^{-1}$; δ(CDCl$_3$) (inter alia) 1.30 (3H, d, J=6.5 Hz), 3.23 (1H, dd), 4.38 (1H, m), 4.76 (1H, d) ppm; λ$_{max}$ (CHCl$_3$) 262 and 334 nm.

EXAMPLE 43

(7S,6R)-7-[1(R)-p-nitrobenzyloxycarbonyloxyethyl]-4-p-nitrobenzyloxycarbonyl-2-thiacephem-3-(3-carbamoylpyridinium)methil bromide

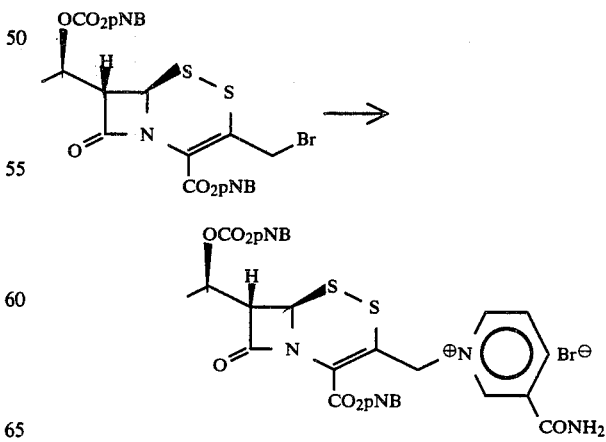

A solution of p-nitrobenzyl (7S,6R)-7-[1(R)-p-nitrobenzyloxycarbonyloxyethyl]-3-bromomethyl-2- thiacephem-4-carboxylate (460 mg) in DMF (5 ml) was stirred overnight in the dark in the presence of nicotinamide (200 mg). Most of the solvent was distilled off and the residue taken up in tetrahydrofuran (150 ml). This solution was repeatedly washed with a solution of NaCl in 0.1N HCl (2×50 ml), with brine (2×50 ml) dried ($Na_2SO_4$) and evaporated. The residue was charged on the top a column packed with silanised silica gel (Merck, Art. 7719). Excess nicotinamide and impurities were eluted with EtOAc, then the product was collected by eluting with EtOAc-HOAc (9:1). Evaporation in vacuo left the title product; $\nu_{max}$ ($CHCl_3$) 1800, 1725, 1695 $cm^{-1}$; δ(deuteroacetone; 200 MHz) 1.67 (3H, d, J=6.4 Hz, $CH_3$—CH), 4.14 (1H, dd, J=2.5 and 4.7 Hz, CH—CH—CH), 5.30 (1H, d, J=2.5 Hz, CH—CH—S), 5.4–5.7 (7H, m, 2×$CH_2$OAr, $CH_2N^+$, and $CH_3$—CH—CH), 7.7–8.4 (8H, m, Ar), and 8.0, 8.7, 9.5 and 9.7 ppm (each 1H, br s, pyridinium).

Analogously, by using isonicotinamide instead of nicotinamide, there was obtained (7S,6R)-7-[1(R)-p-nitrobenzyloxycarbonyloxyethyl]-4-p-nitrobenzyloxycarbonyl-2-thioacephem-3-(4-carbamoylpyridinium)methyl bromide.

EXAMPLE 44

(6S,5R)-6-[1(R)-hydroxyethyl]-2-(piridinium)methyl penem-3-carboxylate

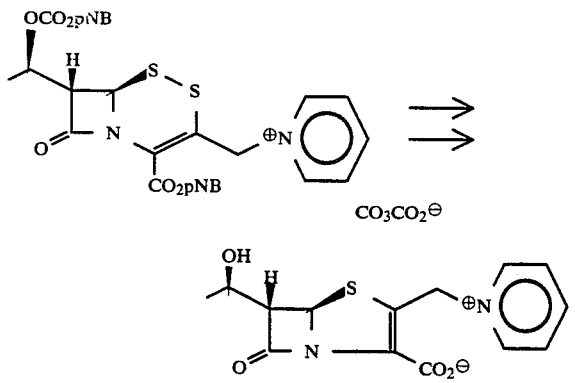

A solution of (7S,6R)-7-[1(R)-p-nitrobenzyloxycarbonyloxyethyl]-4-p-nitrobenzyloxycarbonyl-3-(pyridinium)methyl-2-thiacephem acetate (prepared from the corresponding bromite by conventional treatment with silver acetate or an ion-exchange resin) in chloroform was treated with peracetic acid (2 mol. equivalent) at 0° C. Work-up and gentle heating, according to the general procedure described in Examples 37–39, gave (6S,5R)-6-[1(R)-p-nitrobenzyloxycarbonyloxyethyl]-3-p-nitrobenzyloxycarbonyl-2-(pyridinium)methylpenem acetate; $\nu_{max}$ (KBr) 1795, 1740, 1705 $cm^{-1}$; δ($CDCl_3$+deuteroacetone) 1.4 (3H, d, J=6.5 Hz, $CH_3$—CH), 4.10 (1H, dd, J=1.7 and 8 Hz, CH—CH—CH), 5.20 and 5.31 (each 2H, s, $OCH_2$Ar), 5.2 (1H, m, $CH_3$—CH—CH), 5.77 (1H, d, J=1.7 Hz, CH—CH—S), 6.05 (2H, ABq, J=15 Hz, $CH_2$N), 7.4–8.3 (11H, m, Ar) and 9.15 ppm (2H, d, J=6 Hz, o-Pyr).

This material (300 mg) in tetrahydrofuran-water (1:1, 40 ml) was treated with ammonium chloride (5 g) under stirring to obtain a clear solution.

After cooling to about 10° C., iron powder (2.5 g) was added under vigorous stirring; the reaction could be monitored by TLC ($H_2O$—MeOH—NaCl 9:1:1) by following the development of the product as a faster running spot. After about one hour, celite (3 g) was added and the whole filtered through a glass septum, washing with demineralised water. Removal of the organic solvent, followed by washing with ethyl ether, left an aqueous solution of the title product and inorganic salts.

The former was obtained pure after reverse-phase chromatography and freeze-drying; δ($D_2O$, 200 MHz) 1.27 (3H, d, J=6.5 Hz, $CH_3$CH), 3.98 (1H, dd, J=1.4 and 5.8 Hz, CH—CH—CH), 4.24 (1H, m, $CH_3$—CH—CH), 5.69 (1H, d, J=1.4 Hz CH—CH—S), 5.94 (2H, ABq, J=14.9 Hz, $CH_2N^+$), 8.10 (2H, t, J=6.6 Hz, pyridinium m-H), 8.61 (1H, bd, J=7.7 Hz, pyridinium p-H), 8.95 (2H, d, J=6.6 Hz, pyridinium o-H) ppm.

In a likewise manner, starting from the compounds described in Example 43, there was obtained:

(6S,5R)-6-[1(R)-hydroxyethyl]-2-(3-carbamoylpyridinium)methylpenem-3-carboxylate;

(6S,5R)-6-[1(R)-hydroxyethyl]-2-(4-carbamoylpyridinium)methylpenem-3-carboxylate

EXAMPLE 45

(6S,5R)-6-[1(R)-hydroxyethyl]-2-(1-methyl-1,2,3,4-tetrazol-5-yl)thiomethylpenem-3-carboxylic acid, sodium salt

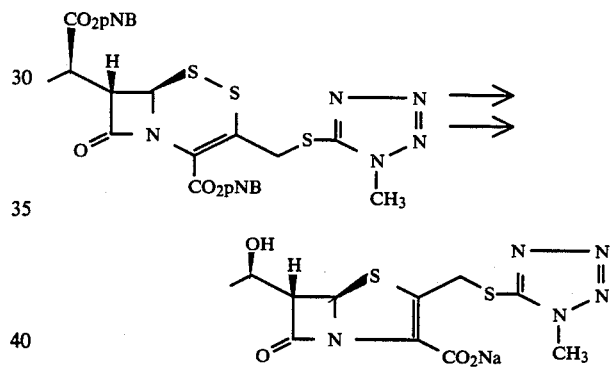

A solution of p-nitrobenzyl (7S,6R)-7-[1(R)-p-nitrobenzyloxycarbonyloxyethyl]-3-(1-methyl-1,2,3,4-tetrazol-5-yl)thiomethyl-2-thiacephem-4-carboxylate in chloroformate was oxidized with m-chloropebenzoic acid, as described in Example 37, to give the corresponding sulphone. Without purification, this material was heated at 60° C. in dry distilled tetrahydrofuran under a stream of nitrogen until extrusion of $SO_2$ was complete. Removal of the solvent and silica gel chromatography gave p-nitrobenzyl (6S,5R)-6-[1(R)-p-nitrobenzyloxycarbonyloxyethyl]-2-(1-methyl-1,2,3,4-tetrazol-5-yl)thiomethylpenem-3-carboxylate;

δ($CDCl_3$) 1.48 (3H, d, J=7 Hz, $CH_3$—CH) 3.84 (1H, dd, J=2 and 5.5 Hz, CH—CH—CH), 3.96 (3H, s, $NCH_3$), 4.69 (2H, ABq, J=14 Hz, $CH_2$S), 5.20 (1H, m, $CH_3$—CH—CH), 5.24 (2H, s, $OCH_2$Ar), 5.27 (2H, ABq, J=13 Hz, $OCH_2$Ar), 5.61 (1H, d, J=2 Hz), 7.51 and 7.82 (each 2H, d, J=8 Hz, Ar), 8.02 ppm (4H, d, J=8 Hz, Ar). Reaction of the above material with Fe/$NH_4Cl$, according to the procedure described in Example 44, afforded the title product; δ($D_2O$) 1.28 (3H, d, J=6.5 Hz), 3.87 (1H, dd, J=1.4 and 6.3 Hz, CH—CH—CH), 4.10 (3H, s, $NCH_3$), 4.19 (1H, m, $CH_3$—CH—CH),4.40 (2H, ABq, J=16 Hz, $CH_2$S), 5.59 ppm (1H, d, J=1.4 Hz, CH—CH—S); $\lambda_{max}$ ($H_2O$) 315 nm.

EXAMPLE 46

Methyl (6S,5R)-6-[1(R)-tert-butyldimethylsilyloxyethyl]-2-nitrooxymethylpenem-3-carboxylate

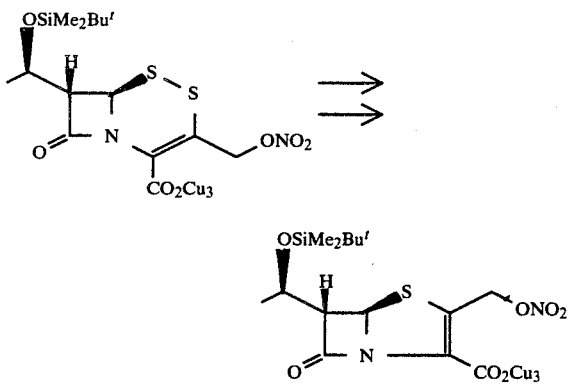

A solution of methyl (7S,6R)-7-[1(R)-tert-butyldimethylsilyloxyethyl]-3-nitrooxymethyl-2-thiacephem-4-carboxylate (prepared as described in Example 31) in chloroform was treated with m-chloroperbenzoic acid (2 molar equiv, 0° C.) to give the 1-sulphone. Aqueous hydrogen carbonate was added to extract m-chlorobenzoic acid, and then the dried organic solution was gently refluxed (t.l.c. monitoring), to give a solution of the title penem compound; $\delta(CDCl_3)$ (inter alia) 5.64 (1H, d, J=2 Hz, CH—CH—S) and 5.65 ppm (2H, ABq, J=15 Hz, sep. of inner line 46 Hz, CH$_2$ONO$_2$); $\nu_{max}$ (CHCl$_3$) 1790 and 1710 cm$^{-1}$. In a likewise manner, starting from trichloroethyl (7S,6R)-7-[1(R)-trichloroethoxycarbonyloxyethyl]-3-nitrooxymethyl-2-thiacephem-4-carboxylate, there was obtained:

Trichloroethyl(6S,5R)-6-[1(R)-trichloroethoxycarbonyloxyethyl]-2-nitrooxymethylpenem-3-carboxylate

EXAMPLE 47

Methyl(6S,5R)-6-[1(R)-tert-butyldimethylsilyloxyethyl]-2-hydroxymethylpenem-3-carboxylate

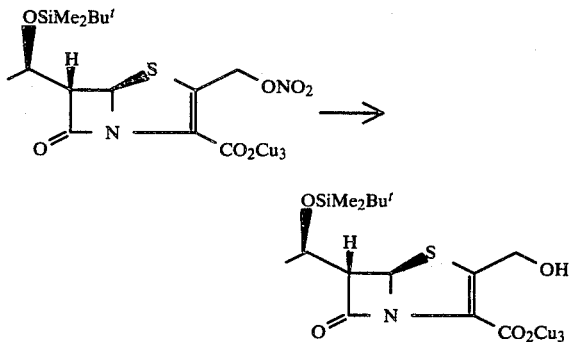

A solution of crude methyl(6S,5R)-6-[1(R)-tert-butyldimethylsilyloxyethyl]-2-nitrooxymethylpenem-3-carboxylate (obtained from 45 mg of the corresponding 3-bromomethyl-2-thiacephem precursor, according to Examples 31 and 46) in dichloromethane (2 ml) was stirred for 5 min at 0° C. with zinc dust (0.1 g) and acetic acid (0.1 ml). The reaction mixture was filtered and the solution was evaporated to give the crude title product, which was purified by silica gel chromatography (ethyl acetate—light petrol, from 1:4 to 1:1); $\nu_{max}$(CHCl$_3$ film) 1785, 1710 cm$^{-1}$; $\delta(CDCl_3)$ 0.07 (6H, s, SiMe$_2$), 0.88 (9H, s, SiBu$^t$), 1.23 (3H, d, CH$_3$—CH), 3.70 (1H, dd, J=1.8 and 4.5 Hz, CH—CH—CH), 4.25 (1H, m, CH$_3$—CH—CH), 4.59 (2H, s, CH$_2$OH) and 5.57 ppm (1H, d, J=1.8 Hz, CH—CH—S).

By operating in an analogous way on trichloroethyl(6S,5R)-6-[1(R)-trichloroethoxycarbonyloxyethyl]-2-nitrooxymethylpenem-3-carboxylate, complete deblocking of the protecting groups was achieved, thus obtaining after aq. NaHCO$_3$ work up and reverse phase chromatography (water as eluant);

(6S,5R)-6-[1(R)-hydroxyethyl]-2-hydroxymethyl-penem-3-carboxylic acid, sodium salt; $\delta(D_2O)$ 1.30 (3H, d, CH$_3$—CH), 3.88 (1H, dd, J=1 and 6.3 Hz, CH—CH—CH), 4.23 (1H, m, CH$_3$—CH—CH), 4.63 (2H, ABq, J=14.5 Hz, separation of inner lines 4 Hz, CH$_2$OH), and 5.62 ppm (1H, d, J=1 Hz, CH—CH—S); $\nu_{max}$ (KBr) 1765 and 1610–1590 cm$^{-1}$.

EXAMPLE 48

(6S,5R)-6-[1(R)-hydroxyethyl]-2-carbamoyloxymethylpenem-3-carboxylic acid, sodium salt

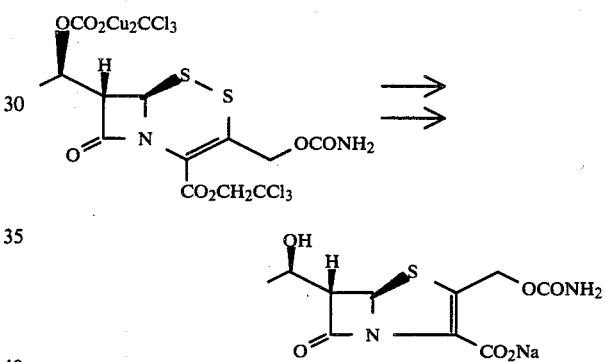

A chloroform solution of trichloroethyl(7S,6R)-7-[1(R)-trichloroethoxycarbonyloxyethyl]-3-carbamoyloxyethyl-2-thiacephem-4-carboxylate was treated with m-chloroperbenzoic acid according to the general procedure of Example 37. After work-up, brief heating of the resulting 1-sulphone in an inert solvent (benzene) gave trichloroethyl(6S,5R)-6-[1(R)-trichloroethoxycarbonyloxyethyl]-2-carbamoyloxymethyl-penem-3-carboxylate; $\delta(CDCl_3)$ 1.5 (3H, d, CH$_3$—CH), 3.94 (1H, dd, J=2 and 8 Hz, CH—CH—CH), 4.73 and 4.82 (each 2H, s, OCH$_2$CCl$_3$), 4.8 (1H, m, CH$_3$—CH—CH) 5.25 (2H, ABq, J=10 Hz, CH$_2$OCONH$_2$), 5.62 (1H, d, J=2 Hz, CH—CH—S).

A THF solution of this material was treated with Zn dust (approx. 6 parts by weight) and 1M aq. NaH$_2$PO$_4$ under stirring. After 3 hours stirring at 25° C., another portion of Zn was added and the mixture kept stirring for 3 hours. Work-up and reverse-phase chromatography afforded the title product; $\delta(D_2O)$ 1.31 (3H, d, J=6.5 Hz, CH$_3$—CH), 3.91 (1H, dd, J=1.5 and 6 Hz, CH—CH—CH), 4.25 (1H, m, CH$_3$—CH—CH), 5.19 (2H, ABq, J=14.5 Hz, CH$_2$OCO) and 5.66 ppm (1H, d, J=1.5 Hz, CH—CH—S).

What we claim is:

1. A process for the preparation of a (5R)-penem derivative of formula I:

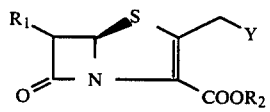

wherein R₁ represents a hydrogen atom, an alkyl group having 1 to 12 carbon atoms, or a cycloalkyl group having 4 to 7 carbon atoms, said alkyl and cycloalkyl groups optionally substituted by hydroxy, protected hydroxy, amino, protected amino, mercapto, protected mercapto or cyano; R₂ represents a hydrogen atom or a carboxy protecting group selected from the group consisting of an alkyl group having 1 to 6 carbon atoms, halo-substituted alkyl group having 1 to 6 carbon atoms, phenyl, substituted phenyl, phenylalkyl wherein the alkyl has 1 to 6 carbon atoms, substituted phenylalkyl wherein the alkyl has 1 to 6 carbon atoms, phenyloxyalkyl wherein the alkyl has 1 to 6 carbon atoms, benzyhydryl, o-nitrobenzhydryl, acetonyl, triimethylsilyl, diphenyl-t-butyl-silyl, dimethyl-t-butyl-silyl, acetoxymethyl, pivaloyloxymethyl and phthalidyl; and Y represents a hydrogen atom, a halogen atom, hydroxy, protected hydroxy, an alkyl group having 1 to 4 carbon atoms, formyloxy, acetoxy, carbamoyloxy, N-alkyl substituted carbamoyloxy, alkoxy having 1 to 4 carbon atoms, 1-pyridinium, carbamoylpyridinium or methyltetrazolylthio; characterized in that a 2-thiacephem derivative of formula II:

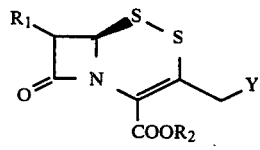

wherein R₁, R₂ and Y are as above defined, dissolved in an inert organic solvent is submitted, at a temperature of from 0° to 60° C., to an oxidative reaction using as oxidizing agent a peracid, to give the corresponding sulphone of formula III:

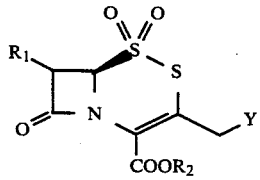

wherein R₁, R₂ and Y are as above defined, which is finally submitted to a desulphurative ring contraction with extrusion of SO₂ by gentle heating in an inert organic solvent or by standing at room temperature so that the desired (5R)-penem derivative of formula I is obtained.

2. A process according to claim 1, wherein R₁ represents alkyl, cycloalkyl or optionally substituted alkyl or cycloalkyl group.

3. A process according to claim 2, wherein R₁ represents a straight or branched alkyl group having from 1 to 12 carbon atoms, which is optionally substituted.

4. A process according to claim 2, wherein R₁ represents methyl, ethyl, or isopropyl optionally substituted with hydroxy or protected hydroxy group, and R₂ is p-nitrobenzyloxycarbonyl, dimethyl-t-butyl-silyl, diphenyl-t-butyl-silyl, trimethylsilyl, 2,2,2-trichloroethoxycarbonyl, benzyl, p-bromophenacy or triphenylmethyl.

5. A process according to claim 2, wherein R₁ represents a monocycloalkyl group having from 4 to 7 carbon atoms, which is optionally substituted.

6. A process according to claim 1, wherein R₂ represents a straight or branched alkyl group having from 1 to 6 carbon atoms, a halo-substituted alkyl group having from 1 to 6 carbon atoms, phenyl or substituted phenyl group, phenyl substituted alkyl group wherein the phenyl is optionally substituted, phenyloxy substituted alkyl group wherein the alkyl has from 1 to 6 carbon atoms, benzhydryl, o-nitrobenzhydryl, acetonyl, trimethylsilyl, diphenyl-t-butylsilyl, dimethyl-t-butyl-silyl, acetoxymethyl, pivaloyloxymethyl or phthalidyl group.

7. A process according to claim 1, wherein Y represents a fluorine, chlorine or bromine atom.

8. A process according to claim 1, wherein Y represents:

(a) hydroxy or protected hydroxy group;

(b) a formyloxy group or an alkanoyloxy group having from 2 to 6 carbon atoms, optionally substituted by a halogen atom, by an alkanoyl group having from 2 to 6 carbon atoms, or by an amino, hydroxy or mercapto group, said amino, hydroxy or mercapto group optionally protected;

(c) an unsubstituted or N-alkyl substituted carbamoyloxy group;

(d) an alkoxy group having from 1 to 4 carbon atoms;

(e) 1-pyridinium or carbamoyl-pyridinium; or (f) a methyltetrazolylthio group.

9. The process according to claim 1 wherein said inert organic solvent is chloroform or benzene and the oxidizing agent is m-chloroperbenzoic acid or peracetic acid.

10. The process according to claim 5 wherein the monocycloalkyl group R₁ is cyclopentyl or cyclohexyl.

11. The process according to claim 6 wherein the alkyl group R₂ is a 2,2,2-trichloroethyl group.

12. The process according to claim 6 wherein the group R₂ is phenyl or p-nitrophenyl.

13. The process according to claim 6 wherein the alkyl group R₂ is substituted with a benzyl group, a p-nitrobenzyl group, or a p-methoxy benzyl group.

14. The process according to claim 6 wherein the alkyl group R₂ is substituted with a phenoxymethyl group.

* * * * *